Figure 1:
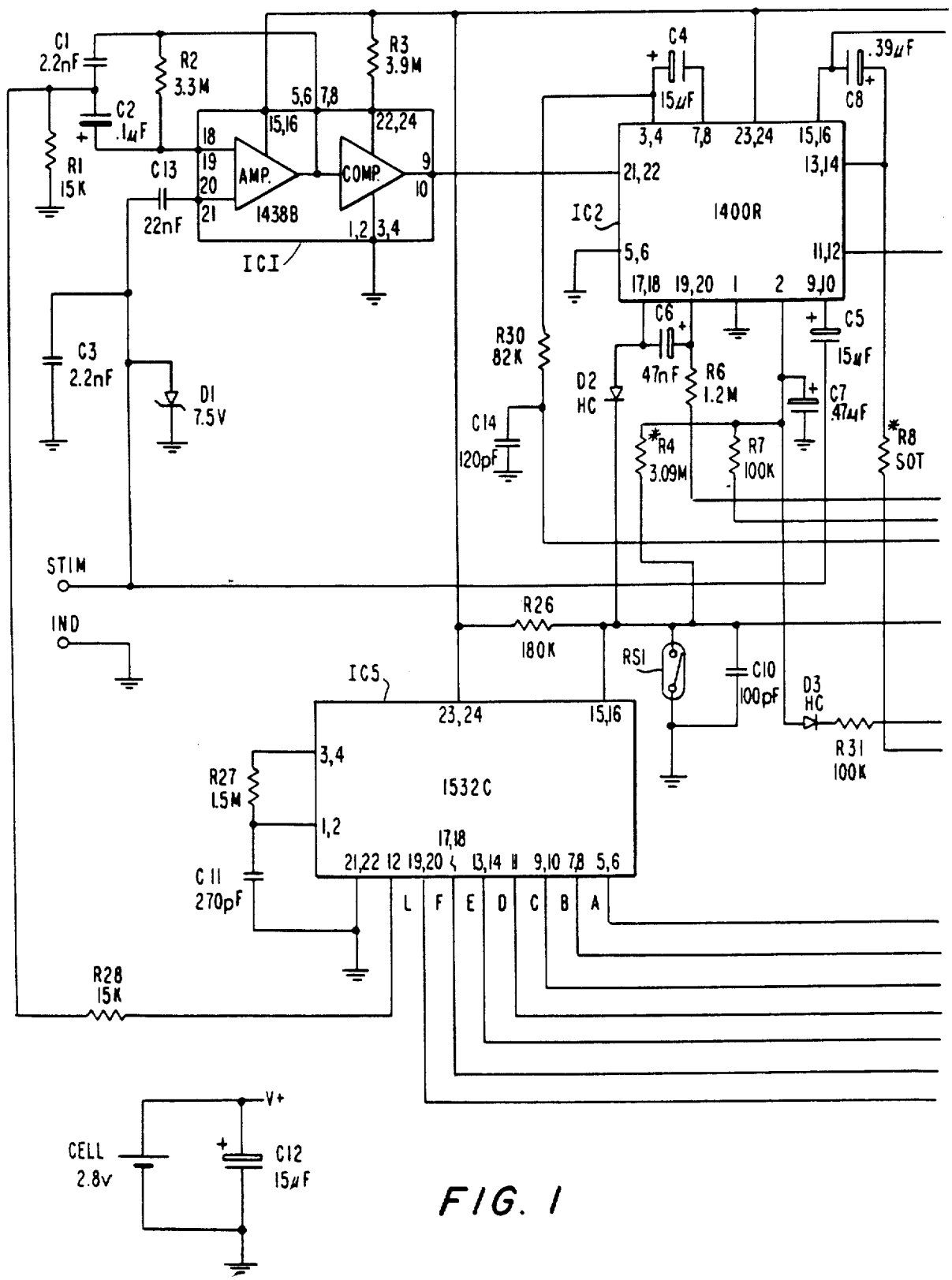

United States Patent [19]

Nappholz et al.

[11] Patent Number: 4,488,553
[45] Date of Patent: Dec. 18, 1984

[54] EXTERNALLY CONTROLLED TACHYCARDIA CONTROL PACER

[75] Inventors: Tibor A. Nappholz, Drummoyne; Stephen J. Swift, Hornsby, both of Australia

[73] Assignee: Telectronics Pty. Ltd., Lane Cove, Australia

[21] Appl. No.: 402,026

[22] Filed: Jul. 26, 1982

Related U.S. Application Data

[62] Division of Ser. No. 245,356, Mar. 19, 1981, Pat. No. 4,407,289.

[51] Int. Cl.³ .............................................. A61N 1/36
[52] U.S. Cl. ............................................ 128/419 PG
[58] Field of Search ........................... 128/702–706, 128/419 PG

[56] References Cited

U.S. PATENT DOCUMENTS

| | | | |
|---|---|---|---|
| 3,241,556 | 3/1966 | Zacouto | 128/419 PG |
| 3,646,930 | 3/1972 | Patterson et al. | 128/704 |
| 4,124,031 | 11/1978 | Mensink et al. | 128/419 PG |
| 4,181,133 | 1/1980 | Kolenik et al. | 128/419 PG |
| 4,280,502 | 7/1981 | Baker, Jr. et al. | 128/419 PG |

Primary Examiner—William E. Kamm
Attorney, Agent, or Firm—Gottlieb, Rackman & Reisman

[57] ABSTRACT

A tachycardia control pacer for which placing a magnet over the patient's chest results in the generation of two pulses, the time separation between which is an indication of the battery potential. Application of the magnet in this way also holds the device off, after the two pulses are generated, so that if the device is causing him discomfort the patient can temporarily disable it until the physician can program it off. Application of a magnet to the patient's chest, or programming of the device, resets two scanned inter-pulse time intervals to the values programmed by the physician. The next scanning begins with the programmed time values. In this way the physician, after inducing tachycardia, can verify the programmed time parameters rapidly by observing the patient's ECG waveform, without having to wait several minutes until scanning from the previously retained successful values would otherwise progress to the programmed values.

5 Claims, 17 Drawing Figures

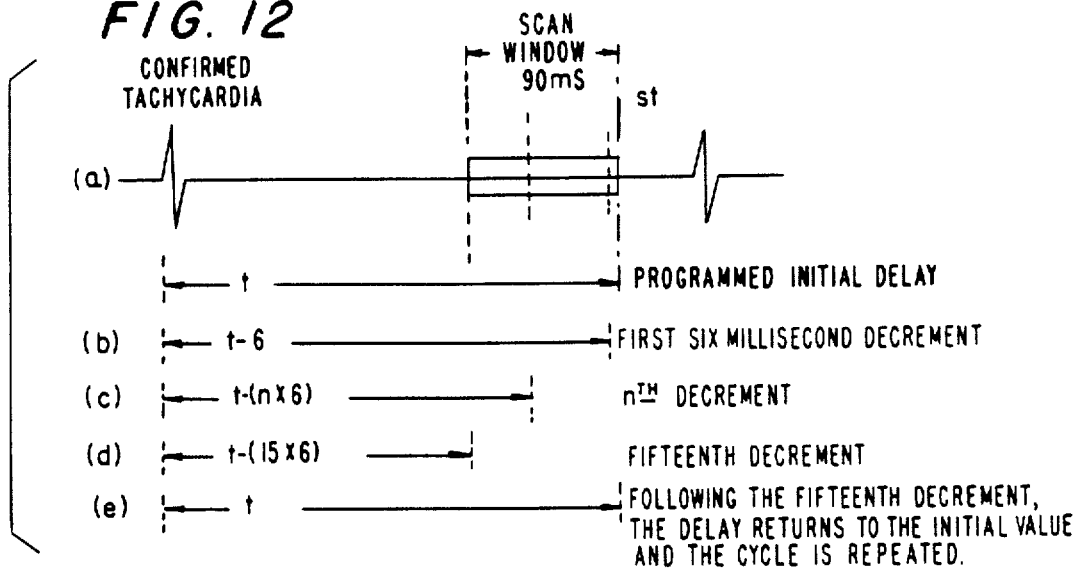
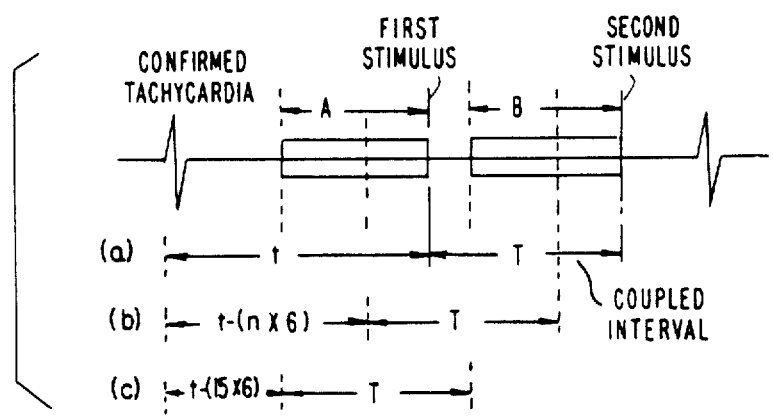
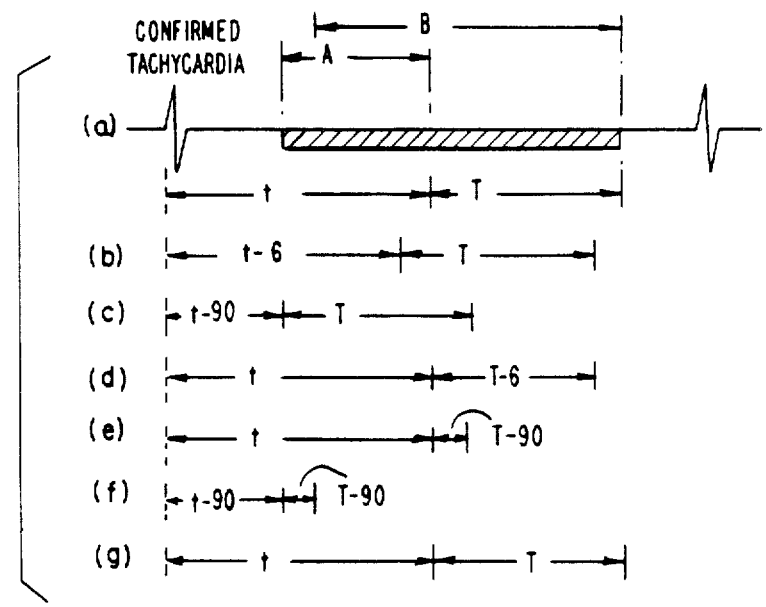

EXTERNALLY CONTROLLED TACHYCARDIA CONTROL PACER

This application is a division of application Ser. No. 245,356, filed Mar. 19, 1981, now U.S. Pat. No. 4,407,289.

This invention relates to tachycardia control pacers, and more particularly to such pacers which can be externally controlled (other than during programming).

Tachycardia is a condition in which the heart beats very rapidly, typically, above 150 beats per minute. There are several different pacing modalities which have been suggested for termination of tachycardia. The underlying principle in all of them is that if a pacer stimulates the heart at least once shortly after a heartbeat, before the next naturally occurring heartbeat at the rapid rate, the heart may successfully revert to sinus rhythm. Tachycardia is often the result of electrical feedback within the heart; a natural beat results in the feedback of an electrical stimulus which prematurely triggers another beat. By interposing a stimulated heartbeat, the stability of the feedback look is disrupted. As with conventional heart pacers, the electrodes of a tachycardia control pacer may be atrially-coupled or ventricularly-coupled. Although the detection of atrial beats and atrial stimulation are preferred, ventricular beat detection and pacing may also be employed.

The difficulty in tachycardia control is that there is usually no way of knowing exactly when a stimulating pulse should be applied. It must be applied shortly after a heartbeat and prior to the time when the next premature beat would otherwise occur, but there is usually only a short period of time somewhere between successive beats during which the generation of a stimulating pulse will successfully terminate tachycardia. In Spurrell-Allen-Kenny U.S. Pat. No. 3,942,534, entitled "Device for Terminating Tachycardia" and issued on Mar. 9, 1976 (corresponding to British Pat. No. 1,493,353 dated Nov. 30, 1977), there is disclosed a pacer which, following detection of tachycardia, generates a stimulus after a delay interval. If that stimulus is not successful in terminating the condition, then another stimulus is generated after another premature heartbeat following a slightly different delay. The device constantly adjusts the delay interval by "scanning" through a predetermined delay range. Stimulation ceases as soon as the heart is restored to sinus rhythm. If successful reversion is not achieved during one complete scan, then the cycle is repeated.

The above-identified Spurrell et al patent further teaches the generation of a second stimulus following the first, both stimuli occurring within the tachycardia cycle, i.e., before the next naturally occurring rapid beat. It has actually been found that the second stimulus may be more effective than the first. As used herein, the time period between a heartbeat and the first stimulus is referred to as the "initial delay", and the time period between the first stimulus and the second stimulus is referred to as the "coupled interval". In the Spurrell et al device, although the coupled interval may be set by the physician, it is fixed once it is set; the second stimulus always occurs a predetermined time after the first stimulus, no matter when the first stimulus occurs after the last heartbeat.

In Spurrell-Nappholz-Swift application Ser. No., filed on even date herewith and entitled "Two-Pulse Tachycardia Control Pacer" (corresponding to British application Ser. No. 8010013, filed on Mar. 25, 1980 and entitled "Heart Stimulating Device"), which application contains the same detailed disclosure contained herein, there is claimed a tachycardia control pacer in which the time intervals which are successful in terminating tachycardia are permanently stored so that, no matter when the next tachycardia episode occurs, the scanning begins with the most recent successful time parameters. While this is no guarantee that the first pair of stimuli will necessarily result in successful tachycardia termination, on average it takes many fewer stimuli to achieve successful reversion because the scanning always being with the last successful time parameters. Also, there is claimed the scanning of the coupled interval, as well as the scanning of the initial delay. Be registering the successful coupled interval as well as the successful initial delay and using the two retained parameter values first when the next tachycardia episode is detected, there is a much greater likelihood of success with the first pair of stimuli the next time they are required.

The tachycardia control pacer claimed in the Spurrell-Nappholz-Swift application is programmable; using conventional heart pacer programming techniques, the physician can program several parameters. Among these are the initial delay and coupled interval values at extreme ends of the respective scans. Since the scanning of both parameters occurs in fifteen 6-millisecond steps, programming of the two extreme values determines the entire range through which each scan takes place. The selection of parameter values is facilitated by externally controlling the pacer to actually induce tachycardia. By allowing the physician to induce the condition and then to monitor the patient to see the effect of different parameter values, optimum values can be programmed for each individual patient. Thus the tachycardia control pacer can actually be operated in a mode, under external control, which induces tachycardia, following which the physician can observe whether the device successfully terminates the condition rapidly with the programmed parameter values.

A conventional heart pacer is often designed so that placing a magnet over the chest of a patient, in the vicinity of the pacer, controls continuous pacing at a rate which reflects the battery potential; this allows the remaining life of the pacer to be ascertained. This is not feasible in the case of a tachycardia control pacer, however, because the device does not function to generate continuous pulses. It is therefore an object of our invention to provide a mechanism for a tachycardia control pacer which allows determination of the battery potential.

It has also been found that at times a patient may experience discomfort from the operation of a tachycardia control pacer. It is another object of our invention to provide a simple mechanism by which a patient can control temporary turnoff of such a pacer, until the physician can program it off.

It sometimes happens that a physician does not know the programmed values for initial delay and coupled interval. This is especially true if a patient visits a new physician. The programmed values can be determined if the physician, after inducing tachycardia, observes the patient's ECG waveform and waits until the scanning sequence reaches the point at which the maximum time values are employed during a cycle. This can often take several minutes. It is therefore another object of our invention to provide a mechanism by which a physician can rapidly determine the programmed values.

All of the aforesaid objectives are accomplished by operating a reed switch (the same reed switch which is operated by the external programmer) while a magnet is placed over the chest of the patient in the vicinity of the pacer. Operation of the switch turns off the pacer so that the patient can temporarily hold the device off while he travels to his physician in order to have the physician program the device off. But before the device turns off it generates two pulses, the time separation between which is a measure of the battery potential. Thus the physician can use a magnet to "turn off" the device for the purpose of generating these two pulses.

If he observes the ECG waveform of the patient and times the interval between the two pulses which are actually generated before the device is turned off, he will be able to ascertain the battery potential.

The same mechanism which responds to the external magnet (or the external programmer) also resets the scanning cycling so that the next cycle utilizes the programmed values of initial delay and coupled interval. Consequently, by resetting the scanning cycling (either by using an external magnet or an external programmer), the physician can control the scanning to begin with the programmed values. Immediately following the inducing of tachycardia, the physician can observe the programmed values on the patient's ECG waveform.

Figure 2:
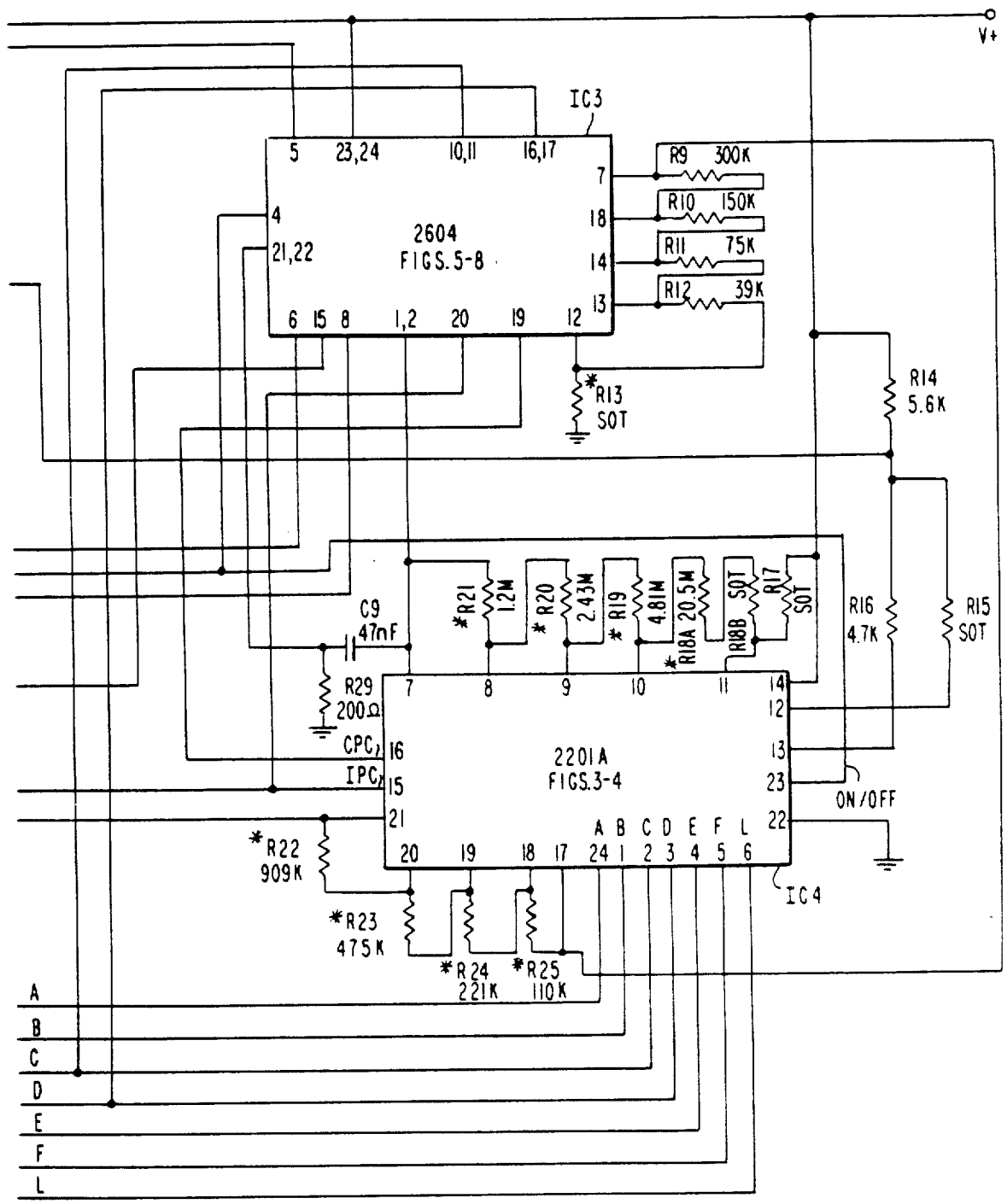
Figure 3:
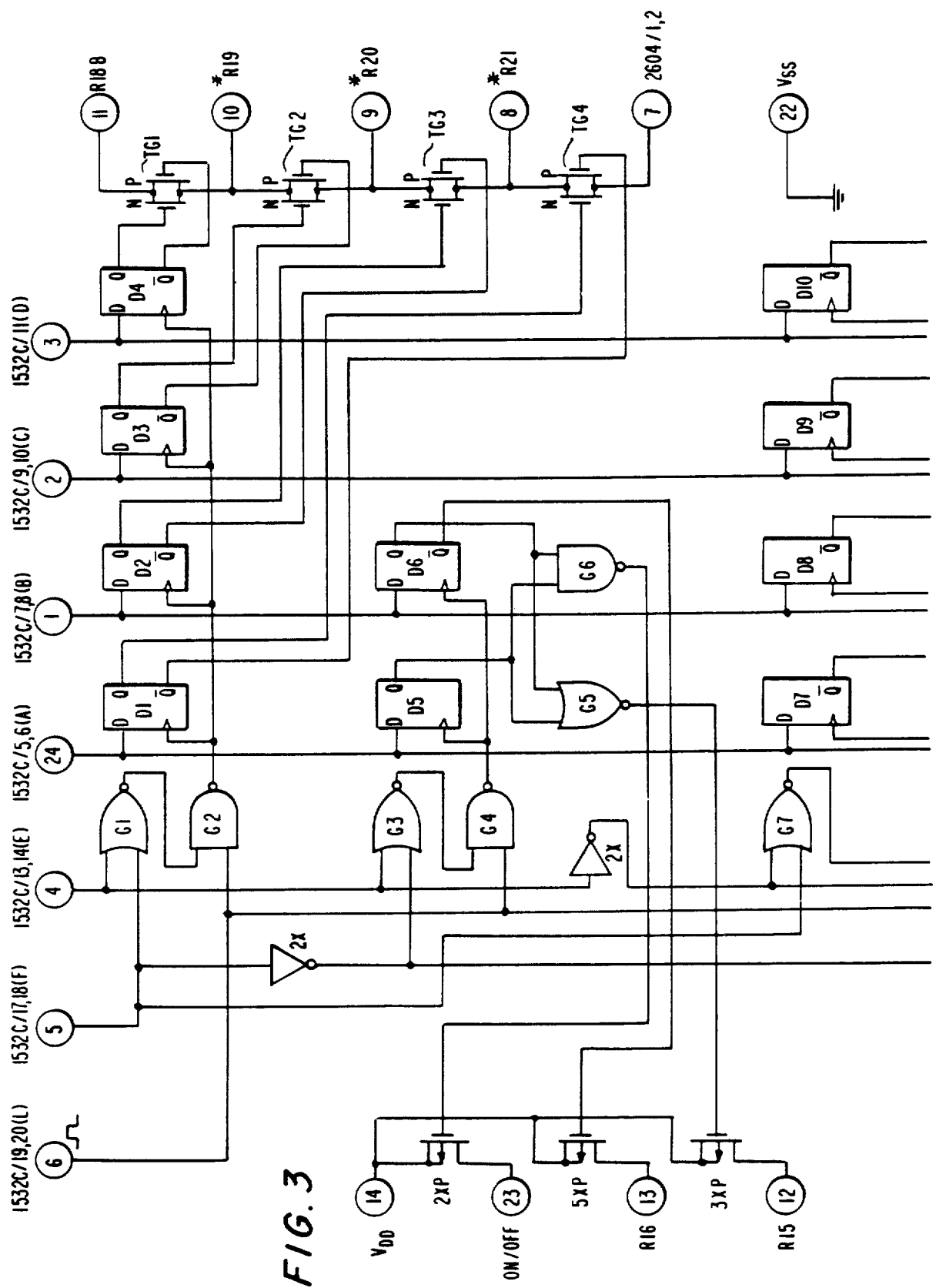
Figure 4:
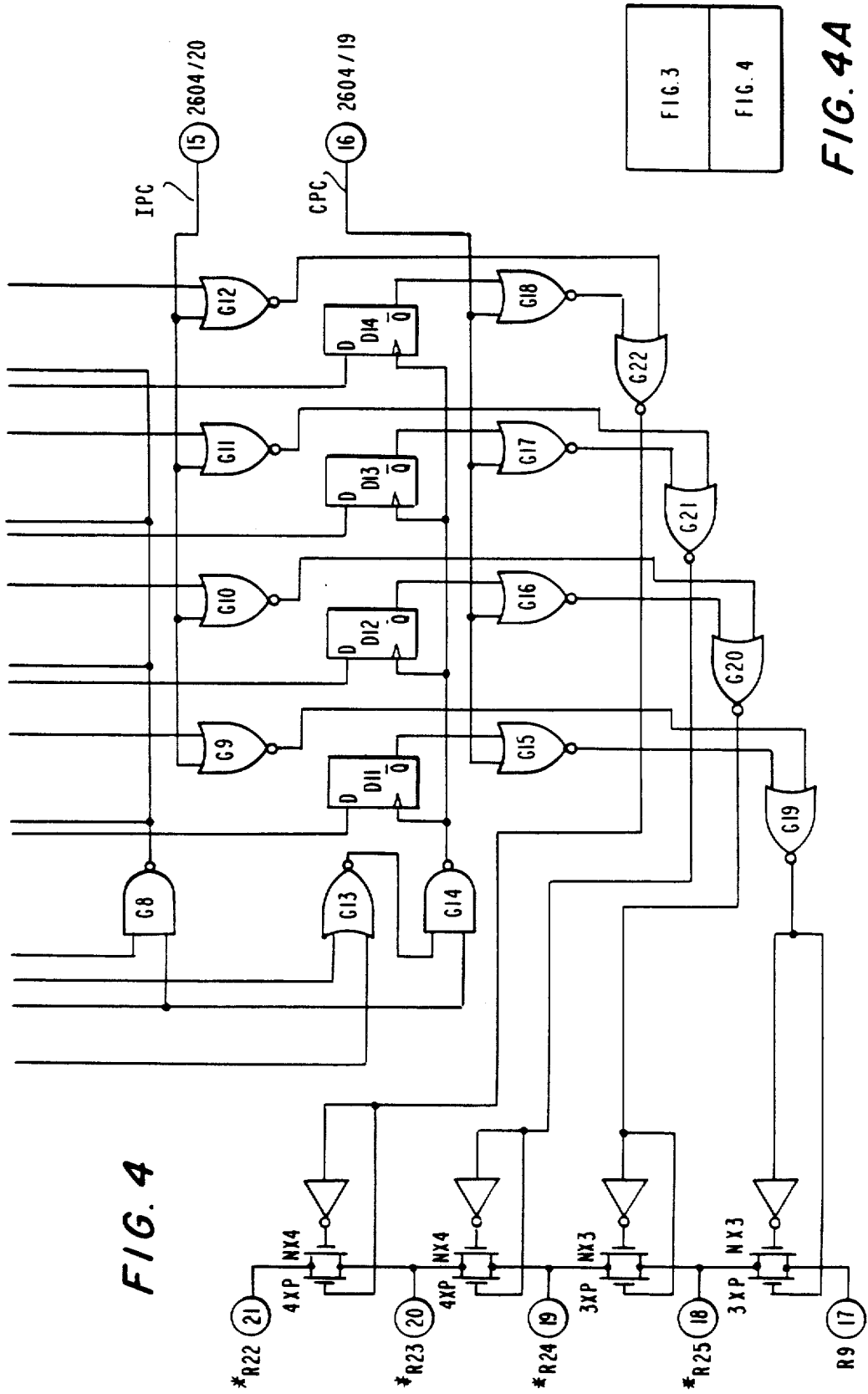
Figure 6:
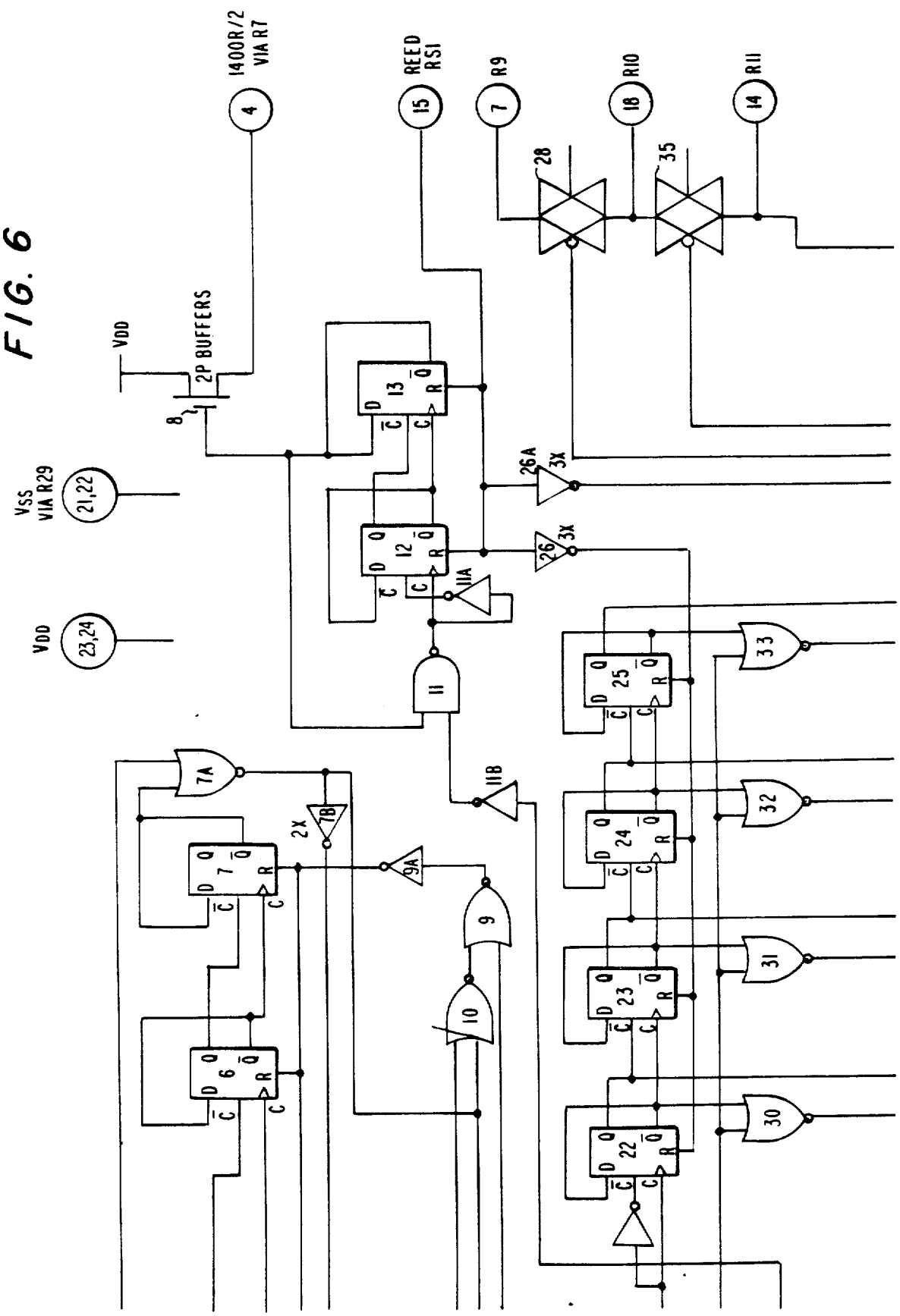
Figure 7:
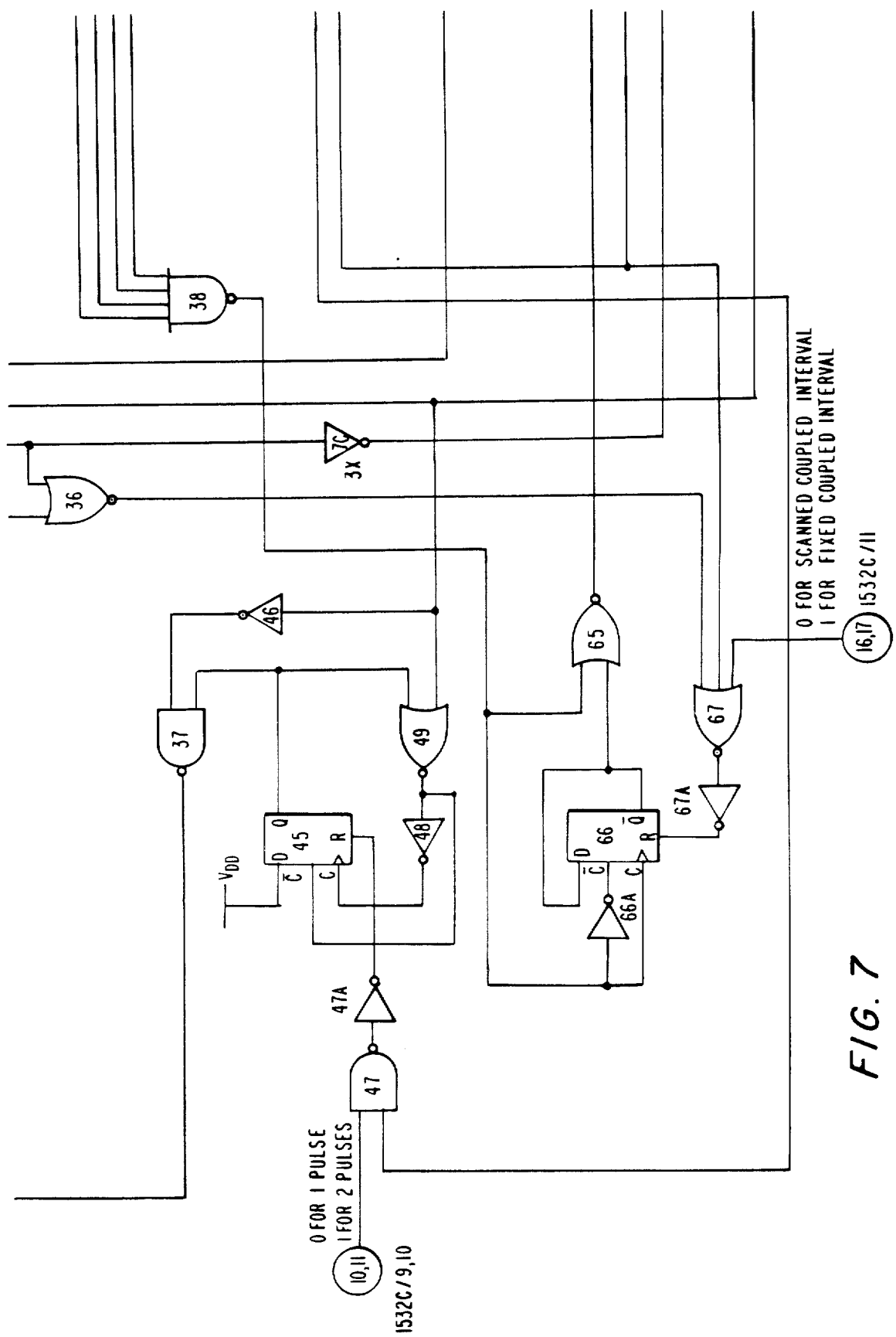
Figure 8:
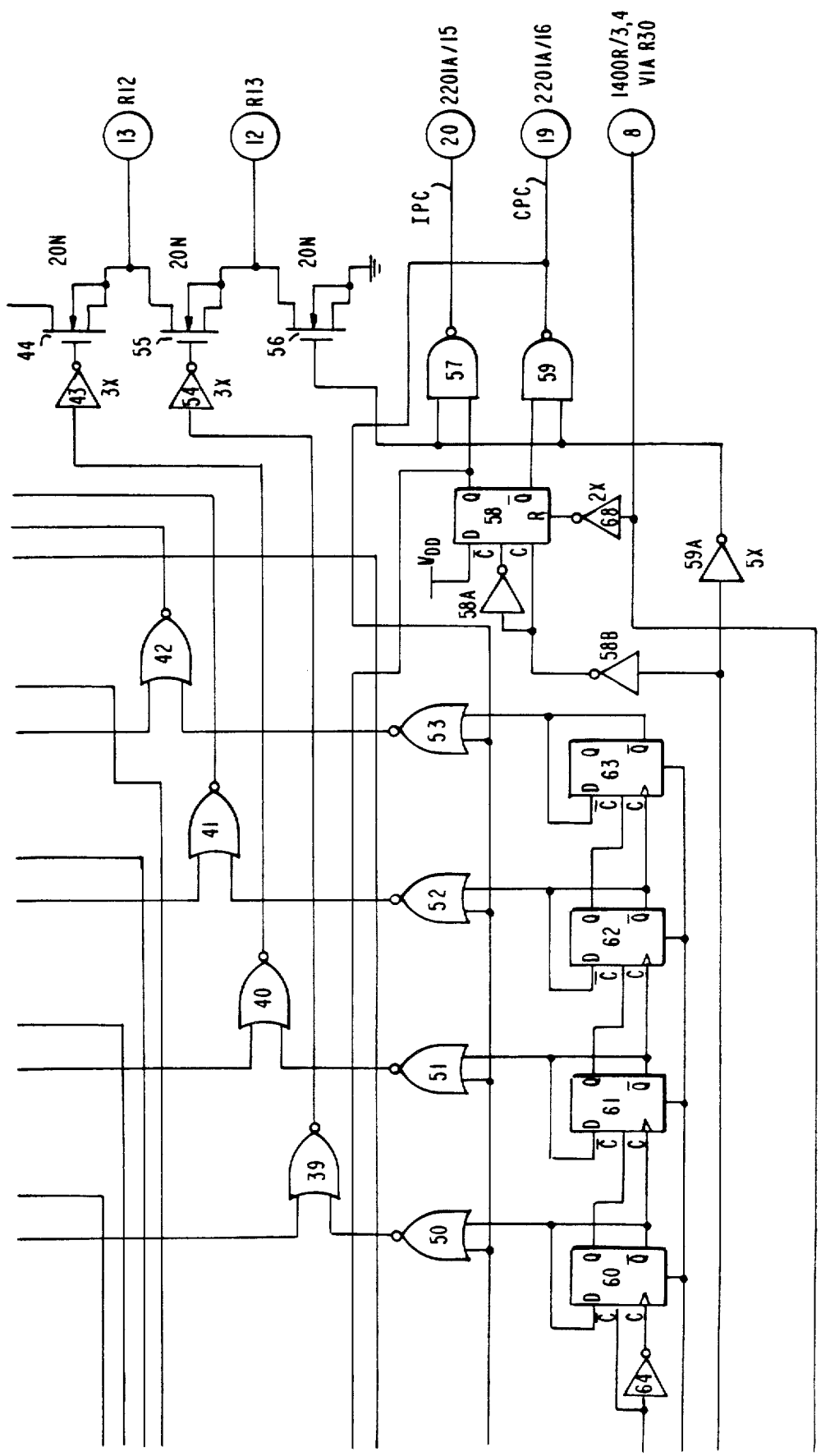

Further objects, features and advantages of our invention will become apparent upon consideration of the following detailed description in conjunction with the drawing, in which:

FIGS. 1 and 2, arranged as shown in FIG. 2A, depict the illustrative embodiment of our invention;

FIGS. 3 and 4, arranged as shown in FIG. 4A, depict the circuitry contained in chip IC4 of FIG. 2;

FIGS. 5-8, arranged as shown in FIG. 8A, depict the circuitry contained in chip IC3 of FIG. 2.

Figure 5:
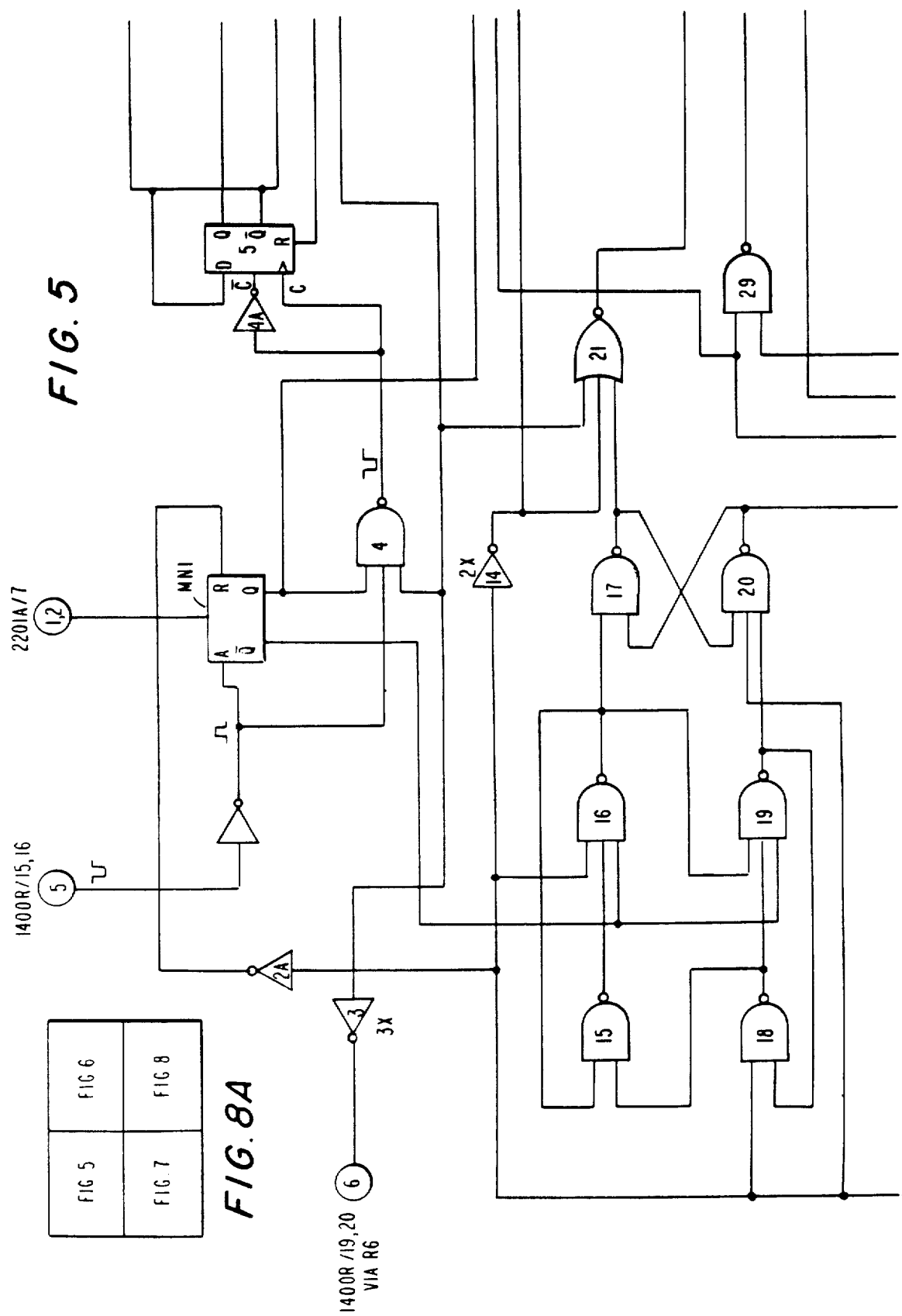
Figure 9:
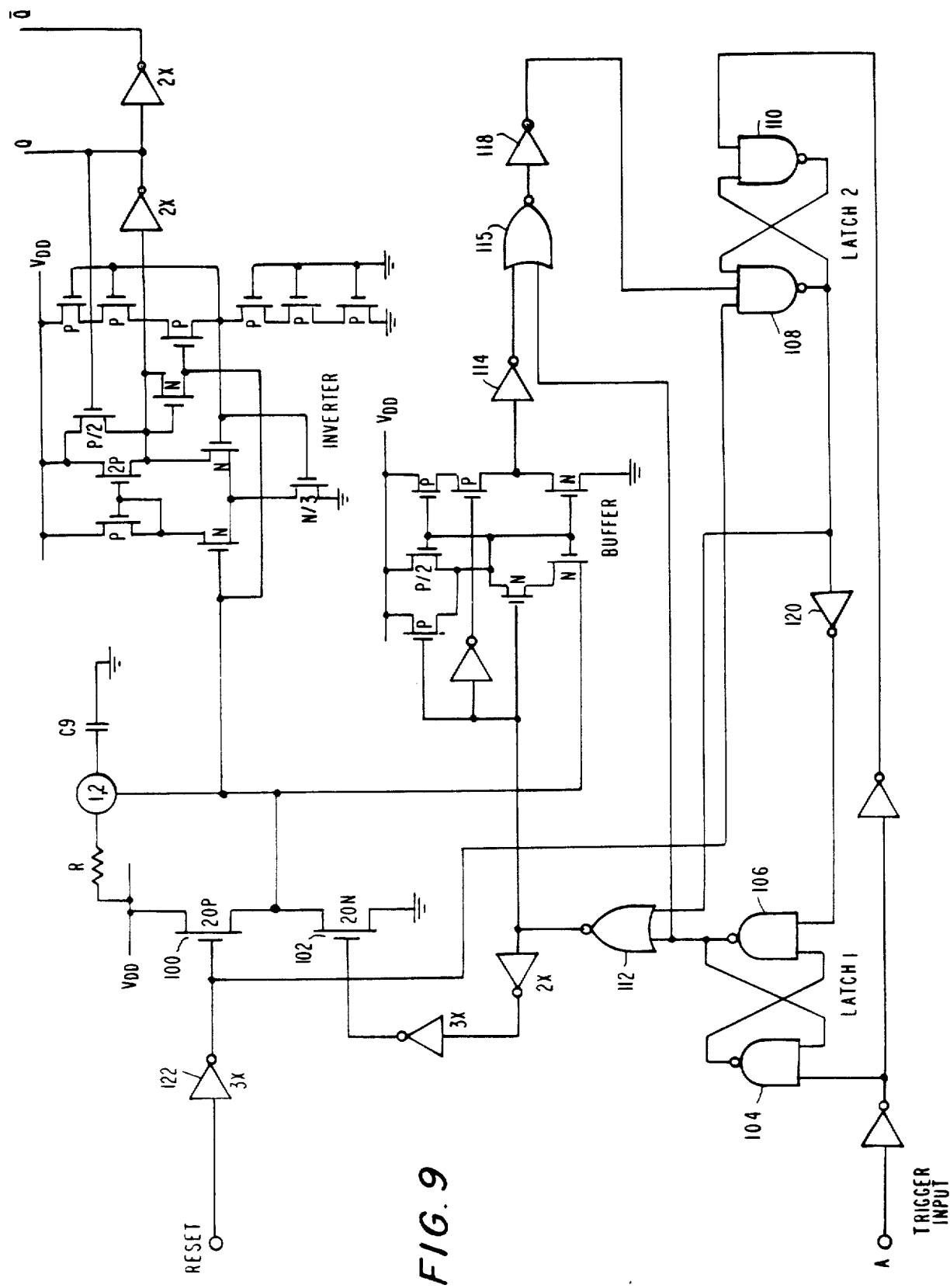

FIG. 9 depicts the details of monostable multivibrator MN1 which is shown only in block form on FIG. 5; and FIGS. 10-14 depict timing waveforms which will facilitate an understanding of the pacer operation.

TIMING WAVEFORMS: FIGS. 10-14

For an understanding of the invention, it is better to begin with what the pacer does rather than how it does it. For this reason, the timing waveforms of FIGS. 10-14 will be described first.

Figure 10:
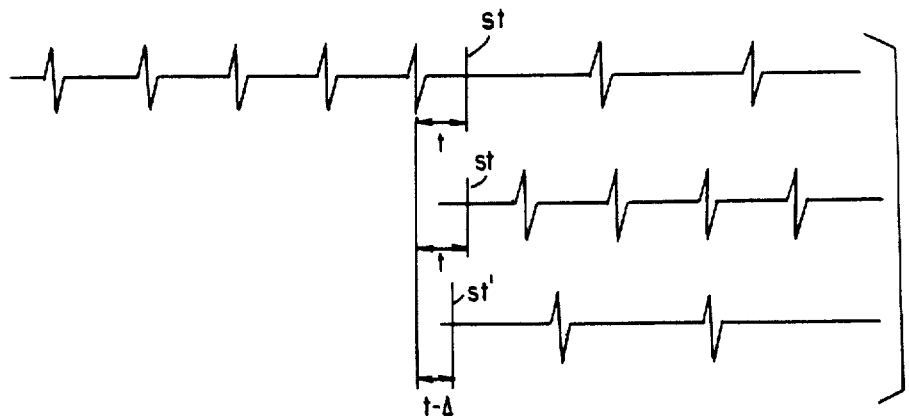

The first waveform in FIG. 10 depicts at the left five heartbeats. In the illustrative embodiment of the invention, a tachycardia episode is detected (referred to as a tachycardia "confirmation") if each of four successive hearteats occurs within a predetermined time interval following the preceding respective heartbeat. (This time interval may be programmed by the physician, as will be described below.) It is presumed that the first beat in FIG. 10 occurred after the preceding heartbeat (not shown) by more than the predetermined interval, but that the four interbeat intervals following this heartbeat were all too short. Upon detection of the fifth heartbeat in the sequence, a tachycardia episode is assumed to be in progress. The upper waveform shows a single stimulus st being deliverd t seconds after the last heartbeat in the sequence, t seconds corresponding to the initial delay. The upper waveform depicts a reversion to sinus rhythm as a result of the single stimulus, with the succeeding heartbeats being separated by more than the predetermined interval which controls tachycardia confirmation. The second waveform in FIG. 10 depicts the application of the same single stimulus, which in this case does not result in tachycardia reversion; it is seen that the succeeding heartbeats are still too rapid.

The last waveform in FIG. 10 depicts (not to scale) the application of a single stimulus st after the fifth hearbeat which comprises a tachycardia confirmation cycle, following an initial delay which is shorter than t milliseconds by $\Delta$ milliseconds. In the illustrative embodiment of the invention, the value of $\Delta$ is six milliseconds. The third waveform simply illustrates what is meant herein by decrementing the initial delay by the decrement value. The initial delay is reduced by six milliseconds from cycle to cycle, as will be described below. In the last case of FIG. 10, the stimulus which followed the shorter initial delay is shown as having been successful in terminating tachycardia.

Figure 11:
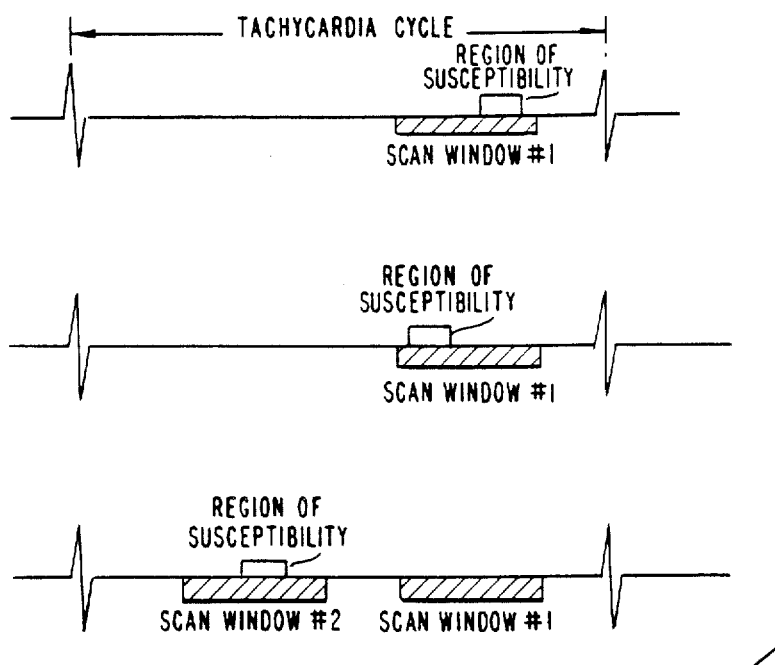

While FIG. 10 depicts a single stimulus as being successful or unsuccessful in terminating tachycardia, it does not show how the initial delay is varied over its entire range, nor does it depict a second stimulus at all. The actual sequencing of the pacer of our invention will be described with reference to FIGS. 12-14. But before proceeding to the actual sequencing, it will be helpful to understand the mechanism by which a stimulus can terminate tachycardia. The top waveform in FIG. 11 shows two heartbeats in a tachycardia cycle (the scale being expanded relative to that of FIG. 10). The pacer of our invention controls a "scan window" between the two heartbeats. The window is 90 milliseconds in duration. It is assumed that a stimulus somewhere within the scan window will be effective in terminating tachycardia; the exact position within the window where the occurrence of a stimulus will be successful may be anywhere within a small range referred to as the "region of susceptibility". If the region of susceptibility is that shown in the upper waveform of FIG. 11, then a stimulating pulse which occurs in this region will be successful in terminating tachycardia. On the other hand, if the region of susceptibility is toward the beginning of the scan window, as shown in the middle waveform of FIG. 11, then it is only a pulse within this region—closer in time to the last heartbeat—which will result in success.

The physician programs the pacer with an initial delay value which is the time between the last heartbeat in the tachycardia confirmation cycle and the right end of the scan window (scane window No. 1 in the two upper waveforms of FIG. 11). It is assumed that the region of susceptibility is somewhere within the scan window, although exactly where is not known; that is why the first stimulus is generated after an initial delay which is different from cycle to cycle.

The bottom waveform in FIG. 11 depicts the case in which the region of susceptibility is not within scan window No. 1. In such a case, the generation of a stimulus at no position within this scan window will result in reversion. It is assumed, therefore, that there is some other scan window which contains a region of susceptibility, this window being shown as scan window No. 2. The physician can program the device to place the 90-millisecond scan window at a selected position after the last heartbeat which confirms tachycardia. Thereafter, the pacer automatically generates stimuli in succeeding cycles (corresponding to a single cycle as shown in FIG 10) in different potential regions of susceptibility; the initial delay is always decremented by 6 milliseconds from cycle to cycle (except in going from the minimum initial delay to the maximum, at the start of a new scan), but the physician does have control over the scan window.

This is shown in greater detail in FIG. 12, which depicts the cycling of the pacer but where a second stimulus is still not generated during each cycle. Following the confirmation of tachycardia, only a single stimulus is generated. The pacer then assumes that the heart is beating normally and determines that another stimulus is required only if tachycardia is once again confirmed by counting four rapid heartbeats, following which another single stimulus is generated during the next cycle.

Waveform (a) in FIG. 12 depicts a single cycle. The interval t represents the initial delay programmed by the physician; in the illustrative embodiment of the invention the initial delay is the maximum delay during any scan. Thus the first stimulus which is generated, during the first cycle, is shown by the symbol st and occurs t milliseconds after the last heartbeat in the confirmation sequence.

Waveform (b) in FIG. 12 depicts the occurrence of the stimulus during the next overall cycle. It must be borne in mind that the next cycle occurs only after tachycardia is confirmed all over again without a reversion to sinus rhythm. In this case, the initial delay is (t-6) milliseconds, and the stimulus depicted in waveform (b) represents the stimulus which occurs following the first 6-millisecond decrement. The stimulus occurs, of course, within the 90 millisecond scan window.

Waveform (c) shows the occurrence of the stimulus after the initial delay has been decremented n times. The stimulus still occurs within the scan window, but it now sooner follows the last heartbeat in the confirmation sequence.

Waveform (d) depicts the sixteenth stimulus in an overall scan, after the fifteenth decrement. The stimulus occurs at the start of the scan window. If this stimulus is not successful in terminating tachycardia, then following the next confirmation a stimulus is generated after t seconds have elapsed in the tachycardia cycle; the scanning begins all over again with the maximum (programmed) initial delay, assuming that there has been no reversion to sinus rhythm.

In the illustrative embodiment of the invention, the second stimulus may be omitted altogether, as depicted in FIG. 12. But if it is used, it can be generated after the first stimulus by either a fixed coupled interval (which can be programmed), or after a variable, scanned coupled interval. FIG. 13 depicts the case in which the coupled interval is fixed at T milliseconds and does not vary. Waveform (a) shows the two time interval parameters programmed by the physician, t milliseconds and T milliseconds. The first stimulus in a new scan occurs t milliseconds after tachycardia confirmation, and the second stimulus occurs T milliseconds later. Waveform (b) depicts the scanning of the initial delay, with the initial delay having been decremented n times, or 6n milliseconds. It will be noted that the second stimulus still occurs T milliseconds after the first. Finally, waveform (c) shows the first stimulus occurring after the shortest initial delay, with the second stimulus still occurring after the fixed coupled interval of T milliseconds. It is thus apparent that in the arrangement depicted in FIG. 13, stimuli are generated within the two scan windows depicted by the letters A and B. The first stimulus always occurs within the window depicted by the letter A, and the second always occurs within the window depicted by the letter B; no stimuli are generated following confirmation within the region between windows A and B.

However, if the coupled interval is scanned, i.e., the time between stimuli is varied, there may be no gap between windows A and B during which a stimulus is not generated. Once again, in FIG. 14 the letter t represents the programmed initial delay, and the letter T represents the programmed coupled interval. At the start of a scanning cycle, the maximum time intervals are both utilized. Thus the first stimulus occurs t milliseconds after tachycardia is confirmed, and the second stimulus occurs T milliseconds after the first stimulus. This is shown in waveform (a). The letter A still represents a 90-millisecond interval. For reasons which will become apparent, however, the letter B now represents a longer time "space" in which the second stimulus can occur.

For any given value of coupled interval, the first stimulus is scanned through its respective window. It is only after a complete scan through the 90-millisecond initial delay window that the coupled interval is decremented by 6 milliseconds, and that the new value for the coupled interval is used while another complete scan of initial delay takes place. Waveform (b) shows when the first and second stimuli are generated during the second cycle. The first stimulus is generated 6 milliseconds earlier than was the first stimulus during the preceding cycle. The second stimulus is still generated T milliseconds after the first stimulus. Of course, since the first stimulus now occurs 6 milliseconds earlier, so does the second stimulus. Waveform (c) shows the first and second stimuli which are generated at the end of the scan of the initial delay. It will be noted that the operation described thus far is the same as that depicted in FIG. 13, since the coupled interval is fixed at T milliseconds during the first scan of the initial delay.

Waveform (d) depicts the two pulses which are generated at the start of the next scan of the initial delay. As in waveform (a), the first stimulus is generated t milliseconds after tachycardia confirmation. But the coupled interval is now 6 milliseconds shorter than it was during the first scan of the initial delay. The scanning of the initial delay now takes place in the same way, with the new value of T-6 milliseconds being used for the coupled interval each time. If reversion to sinus rhythm is not achieved, then the coupled interval is decremented once again by 6 milliseconds, the new coupled interval being used for another complete scan of the initial delay.

Waveform (e) depicts the values of the initial delay and the coupled interval at the start of the very last scan of the initial delay. It is assumed that the coupled interval has been decremented down to its lowest value of T-90 milliseconds. Thus at the start of the last scan of the initial delay, the first stimulus is generated t milliseconds after tachycardia confirmation, and the second stimulus is generated T-90 milliseconds later. The initial delay is then decremented by 6 milliseconds during succeeding cycles, while the coupled interval remains fixed at T-90 milliseconds. Waveform (f) depicts the end of the overall scanning sequence with both the initial delay and the coupled interval being at their lowest values. If success is not achieved, then the system starts all over again with the two programmed values, as shown in waveform (g).

It will be observed that the second stimulus in waveform (f) is generated at a time corresponding to the left-most end of time "space" B in FIG. 14. Thus it is apparent that with a maximally flexible system such as that illustrated by FIG. 14, the first stimulus ranges within time "space" or window A, while the second stimulus ranges within a time "space" B, which may or may not overlap time "space" A.

In general, the initial delay should be scanned over at least a 60-millisecond range, and its maximum value should be programmable over at least a range of 150 milliseconds. The coupled interval should similarly be scanned over at least a 60-millisecond range, but its maximum value should be programmable over at least a range of 200 milliseconds.

As will be described in detail below, the actual cycling is slightly different from that depicted in FIG. 14 for two reasons. First, the cycling does not necessarily begin with the two programmed values of t and T. Instead, the two values which were used during the last successful tachycardia termination are the first to be tried, with the cycling then proceeding with the decrementing of the initial delay value as just described. Second, for any value of coupled interval T, there are actually two scans of the initial delay. The cycling begins with the retained t and T values. After the initial delay has been decremented down to its lowest value, the coupled interval is not decremented as implied above. Instead, the programmed initial delay value is used to start another scan of the initial delay, and the previously successful coupled interval value is used during the new scan of initial delay. This is because the first scan of the initial delay does not begin with the programmed initial delay value, but rather with the retained initial delay value. Thus there is only a partial scan of the initial delay and, if it is not successful, it is preferred to provide a complete scan of the initial delay while using the previously successful coupled interval value, just in case the retained coupled interval value will be successful with an initial delay value which is longer than the previously successful initial delay value. It is only after the second initial delay scan that the coupled interval is decremented. It is not necessary thereafter to provide two scans of the initial delay for each new value of coupled interval. Nevertheless, this is what is actually done in the illustrative embodiment of the invention in order to simplify the circuitry. Thus in actual practice what happens is that each time the coupled interval is decremented, there are two scans of the initial delay, and only after the second scan is the coupled interval decremented again by 6 milliseconds.

Monostable Multivibrator: FIG. 9

Chip IC3 on FIG. 2 is the most complex of the five chips IC1-IC5 shown on FIGS. 1 and 2. The details of chip IC3 are depicted in FIGS. 5-8. One of the elements on the chip is multivibrator MN1 on FIG. 5. The operation of the multivibrator, from a system point of view, is very straight-forward. It is a re-triggerable device which generates a positive pulse at its Q output each time a trigger is received at the A input. If another trigger is received before the multivibrator has timed out, the Q output remains high for another timing period. The multivibrator is used to confirm tachycardia, and to understand the system operation the details of the multivibrator are unimportant. In order that the description of the system not be complicated by the details of the multivibrator operation, it would be best to consider the multivibrator at this point so that in the system description the detailed operation of the element can be ignored.

In FIG. 5, multivibrator MN1 is shown as having five inputs/outputs. The Q output is normally low in potential and $\overline{Q}$ output is normally high. A positive potential at the reset (R) input resets the multivibrator in this state. Upon receipt of a positive trigger pulse at the trigger (A) input, however, the Q output goes high and the $\overline{Q}$ output goes low. The duration of the pulse is controlled by various components connected to pins 1 and 2 on chip IC3. (The two pins are shorted to each other.) Referring to FIG. 2, it will be noted that pins 1 and 2 on chip IC3 are connected to capacitor C9, the other end of which is grounded through 200-ohm resistor R29. (The junction of the resistor and capacitor also serves as the $V_{SS}$ connection to chip IC3 at pins 21,22, as shown on FIG 6.) Pins 1 and 2 on chip IC3 are also connected to a resistor chain, the first resistor of which is R21, as shown on FIG. 2. As will be described below, some of the resistors in the chain are shorted depending upon how the pacer has been programmed. But the total impedance determines the programmed "tachy rate", that is, the minimum inter-beat interval which, if exceeded, will abort a tachycardia confirmation cycle.

The multivibrator is shown in detail on FIG. 9. The reset and trigger inputs are shown on the left of the drawing, and the Q and $\overline{Q}$ inputs are shown in the upper right corner. Pins 1 and 2 of chip IC3 are shown connected on FIG. 9 to capacitor C9, just as the pins are shown connected on FIG. 2. However, instead of showing the complete resistor chain on FIG. 9, as it is shown on FIG. 2, the resistor chain is simply shown by a single impedance designated R.

On FIG. 9, $V_{DD}$ represents the battery potential, nominally 2.8 volts. Conventional symbols are employed to represent CMOS P-channel and N-channel enhancement-mode transistors, with designations such as P/2 or 2P referring to relative "on" impedances, that is, a 2P device conducts twice as much current as a P device for the same gate-source bias. The other devices shown comprise standard CMOS gates; symbols such as 3X adjacent an inverter refer to the fact that three standard inverters are connected in parallel.

In the absence of any trigger inputs, both of transistors 100 and 102 are off. Capacitor C9 charges through the resistor chain symbolized by the single resistor R from the positive supply, and pins 1 and 2 are at a high potential. The various devices which comprise the "inverter" function as a comparator. The 6 P-channel devices connected in series derive a threshold voltage which is equal to about half of the supply voltage. This threshold voltage is compared with the potential at pins 1 and 2. As long as the potential at pins 1 and 2 exceeds the threshold voltage, the Q output is low (thus the terminology "inverter", although the circuit also functions as a comparator). It is only when the capacitor voltage is less than the threshold voltage that the Q output is high and the $\overline{Q}$ output is low.

As will be described below, the trigger inputs represent heartbeats. The trigger input is normally low in potential. Gates 104,106 comprise a first latch, and gates 108,110 comprise a second latch. After the multivibrator times out, the output of latch 1 (output of gate 106) is high in potential and the output of latch 2 (output of gate 108) is low in potential. Latch 1 is considered to be reset, and latch 2 is considered to be set.

When a heartbeat is detected, the positive pulse at the trigger input causes latch 1 to set and the output of gate 106 goes low. Because both latch outputs are now low, and the two opposite are connected to the inputs of gate 112, its output now goes high. After being inverted twice, the high output of gate 112 causes transistor 102 to turn on. This has the effect of causing capacitor C9 to rapidly discharge through the device; the Q output now goes high and the $\overline{Q}$ output goes low.

The elements which comprise the "buffer" are a form of comparator, and they serve to detect when the capacitor voltage drops to about 100 millivolts. As long as the capacitor voltage exceeds 100 millivolts, the input to inverter 114 is low in potential. One input of gate 115 is thus high and the output of inverter 118 is similarly high; it is this high potential which holds latch 2 set with the output of gate 108 being low, as originally assumed. The second input of gate 115 is connected to the output of gate 106 which is also originally high. Thus in the absence of any heartbeats, both inputs to gate 115 are high, latch 2 remains set, and latch 1 remains reset. Even after a heartbeat is detected and the output of gate 106 goes low, latch 2 remains set because the output of inverter 114 is still high.

But as soon as capacitor C9 discharges through transistor 102 to the point at which its potential drops to 100 millivolts, the output of inverter 114 goes low. Since latch 1 is now set with the output of gate 106 also being low, the output of inverter 118 goes low. This causes latch 2 to reset, with the output of gate 108 going high. The high potential at the output of gate 108 causes the output of gate 112 to go low, and immediately causes transistor 102 to turn off. The high potential at the output of gate 108 is also inverted by inverter 120 to reset latch 1, with the output of gate 106 going high once again. The high potential at the output of gate 106 now sets latch 2 once again (or as soon as the trigger pulse terminates), since the output of gate 106 is connected to an input of gate 115. Consequently, latch 2 is set once again in its quiescent condition just as latch 1 is reset in its quiescent condition. Although the output of gate 108 no longer holds transistor 102 off, it is now the high output of gate 106 which holds the transistor off. The capacitor now starts to charge once again through the resistor chain.

It is thus apparent that following each heartbeat and the discharge of capacitor C9, the Q output of the multivibrator goes high and the $\overline{Q}$ output goes low. As soon as the capacitor charges to the threshold level of the inverter, in a time dependent upon the magnitude of impedance R, the output pulse terminates and the Q output goes low once again with the $\overline{Q}$ output going high. But if another heartbeat is detected before the capacitor can charge to the threshold level, the charging cycle begins all over again as soon as the capacitor discharges through transistor 102, and the Q output remains high. Thus the Q output remains high as successive heartbeats are detected, without going low between them, only if the heartbeats are detected at a rate fast enough to prevent capacitor C9 from charging to the threshold voltage of the "inverter". The multivibrator is re-triggerable in the sense that each trigger input extends the output pulse (positive potential at the Q output) for another time-out interval. As will be described below, this is the basic mechanism for detecting a tachycardia episode—as long as four heartbeats are detected after an initial triggering of the multivibrator, without the Q output of the multivibrator going low, then it is assumed that a tachycardia episode has been detected. If any pair of successive heartbeats are separated by a time interval which exceeds that required for capacitor C9 to charge to the threshold level, then the Q output of the multivibrator goes low. As will be described below, this aborts the tachycardia confirmation counting cycle. by programming the value R, the physician can determine the heartbeat rate which if exceeded will result in tachycardia detection. The effective rates which the physician can program vary between 130 and 225 beats per minute. (As will be described below, the physician can also "fool" the pacer by programming it to a "tachy rate" of only 40 beats per minute; this results in the pacer treating normal beats as a tachycardia episode, the pacer automatically generates "premature" stimuli in an effort to terminate non-existing tachycardia and this may actually induce real tachycardias. By then reprogramming the pacer with a normal "tachy rate", the physician can check whether the programmed time parameters are effective in terminating tachycardia.)

The reset input on FIG. 9 is normally low in potential. The high output of inverter 122 holds transistor 100 off and also holds one input of gate 108 high so that latch 2 can operate as described above. But when the reset input is high, as will be described below, the output of inverter 122 is low in potential and transistor 100 turns on. This has the effect of rapidly charging capacitor C9 through transistor 100 from the $V_{DD}$ supply, and the Q output of the multivibrator remains low (as though heartbeats were not being detected at all) for as long as the reset input is high. The low input now applied by inverter 122 to one input of gate 108 causes the output of latch 2 to be forced high, and this in turn holds the output of gate 106 high even if trigger pulses are received. In this way, transistor 102 remains off independent of trigger inputs.

The reason for the relatively "complex" multivibrator is that the battery supply, while nominally 2.8 volts, can drop as low as 2.2 volts with age. In order that the time-out remain constant independent of the battery potential, the circuit is designed to provide a threshold which is equal to about half of the battery supply, no matter what its value. This is the function of the six P-channel transistors in the "inverter" circuit. Since the battery potential determines both the level to which capacitor C9 charges and the threshold potential, the time-out is independent of the precise potential level.

It should be noted that this type of multivibrator is standard in the art. In fact, Motorola Inc. markets a component (MC14538) which is just such a multivibrator; its time-out period is independent of supply voltage. But the circuit of FIG. 9 is preferred because it operates on low voltages and draws very little current (thereby extending device life).

Overview Of The System And General Chip Descriptions

The overall system is shown on FIGS. 1 and 2, and it includes five chips IC1–IC5. Chips IC1, IC2 and IC5 are standard-type chips used in heart pacers; they will be described below only in terms of their input and output signals, and the functions which they perform. Chips IC3 and IC4 are specially-designed chips and they will be described in detail. The circuitry included on chip IC4 is shown in FIGS. 3 and 4, and the circuitry included on chip IC3 is shown in FIGS. 5–8.

Each of the five chips on FIGS. 1 and 2 is designated not only by one of the labels IC1–IC5, but also by its chip number, e.g., chip IC5 bears number 1532C. On each of the two sets of chip drawings of FIGS. 3 and 4, and FIGS. 5-8, each pin of the respective chip is labeled not only by number, but also by its connection in the overall system. For example, pin 5 of chip IC3 (see FIG. 5) has adjacent to it the designation 1400R/15,16. This means that pin 5 of chip IC3 is connected to pins 15 and 16 of chip IC2 (1400R). Referring to FIGS. 1 and 2, it will be seen that pin 5 of chip IC3 is indeed connected to pins 15 and 16 of chip IC2. As another example, pin 21 of chip IC4 (see FIG. 4) bears the designation *R22. This means that pin 21 of the chip is connected to resistor *R22, as shown in FIGS. 1 and 2.

In FIGS. 1 and 2, it will be noted that several of the resistors have an asterisk preceding their labels; this symbol identifies a resistor as being a high-stability component. Several of the resistors are not provided with component values, and instead are labeled "SOT". Such a designation refers to the fact that the value of the respective component is "selected on test", i.e., a component value is selected which provides proper operation. The component ranges for the resistors designated as SOT are as follows:

R13: 8.06–11.5M
R8: 220–420K
R17: 4.81–8.66M
R18B: 8.2–11.5M
R27: 1.2–2.4M
R15: 3.9–6.8K

It wll also be noted that many of the inputs and outputs of the chips on FIGS. 1 and 2 have two pin designations. For example, IC2 on FIG. 1 is connected to the positive supply rail via two pins 23,24. It is standard practice in the pacer art to provide such double connections for increased reliability; even if one pin connection fails, because the two pins are internally connected on the chip, the chip still functions for its intended purpose as long as the other pin connection remains intact.

Chip IC1 is a conventional sense amplifier/comparator, and chip IC2 is a conventional timing oscillator/pulse doubler; both chips are standard chips used in the manufacture of heart pacers and are available from Amalgamated Wireless Microelectronics Pty. Ltd. of Sydney, Australia. Chip IC5, used by Telectronics Pty, Ltd. in its standard line of heart pacers, is a standard-type "program controller" chip; this chip detects reed closures, as controlled by an external programmer, and sets programmable parameters accordingly in the pacer. Techniques for programming pacers are standard in the industry, the design of program controllers is well known in the art, and there is nothing unique about use of the particular chip No. 1532C insofar as the present invention is concerned; any conventional programming technique may be employed, as long as it provides the signals to be described below. Chip IC4 serves primarily to store programmed values and to control the shorting out of selected resistors in two resistor chains. Chip IC3 contains most of the logic which is unique to the present invention.

Programming Of The Pacer: Chips IC4 And IC5, And The Resistor Chains

Before proceeding to a detailed description of the system operation, the manner in which the pacer can be programmed will first be described. In this way, it will be understood how the various latches contain parameter values when the data stored in these latches are described below as controlling respective functions.

The programming is essentially independent of the system operation, and it will be convenient to describe it first so that the pacing functions can be considered below without having to digress for the purpose of describing the programming.

Chip IC5 on FIG. 1 (1532C) is a conventional-type program controller. The $V_{DD}$ connection to the chip is at pins 23,24. (As shown at the bottom of FIG. 1, the positive supply potential, V+, is derived from a 2.8-volt cell, with a filter capacitor C12 connected across it.) Reed switch RS1 is connected to pins 15,16, with resistor R26 serving as the pull-up for the switch. Under the influence of an external magnetic field, the normally-open reed switch is closed, and a ground potential is applied to pins 15,16. Resistor R27 and capacitor C11 are the timing components for an internal oscillator on the chip. Incoming reed pulses must be properly timed if an incoming programming sequence is to be treated as valid; the internal oscillator on the chip determines whether valid programming pulses are received. For example, if the reed switch is held closed for a long time period by placing an external magnet over the chest of the patient, because the resulting pulse at pins 15,16 is too long relative to the oscillator timing, the reed closure has not effect on the outputs of chip IC5.

There are six parameters which may be programmed. The first is pulse width, i.e., the width of each pulse generated by the pacer. Two bits are used to represent the pulse width, and there are thus four possible values. The first value is 0–effectively disabling the pacer since no pulses are generated. The three pulse widths which can be controlled when the pacer is operative are 0.25, 0.35 and 0.6 milliseconds.

The second parameter is sensitivity. A single bit is used to control sensitivity of the same amplifier/comparator chip IC1, as is standard in the pacer art. The two sensitivities are 1 millivolt and 2 millivolts.

The third programmed parameter pertains to the second stimulus which is generated during each pacing cycle. As depicted in FIG. 12, in some cases it may be desired not to have a second stimulus at all. As depicted in FIG. 13, in some cases it may be desired to have a second stimulus which always follows the first stimulus by a fixed (programmed) coupled interval. Finally, as depicted in FIG. 14, in other cases it may be desired to have a second stimulus which follows a coupled interval which is scanned (the maximum coupled interval being programmed). One bit is required to represent whether a second stimulus is generated at all. If it is, another bit represents whether the coupled interval is fixed or scanned.

The fourth parameter is the maximum initial delay value, shown by the letter t on FIGS. 12-14. Scanning of the initial delay begins with this value the first time that the pacer is called upon to terminate tachycardia after the initial programming. (Thereafter, the successful initial delay is retained, and subsequent scanning begins with the retained value.) There are 12 maximum initial delay values from which the physician can choose, and thus four bits are required to represent them. The values are 200, 210, 230, 250, 270, 290, 300 320, 340, 360, 380 and 390 milliseconds.

The fifth parameter which can be programmed is the coupled interval, represented by the letter T in FIGS. 13 and 14. The programmed value serves no function if the pacer is programmed not to generate a second stimulus at all. But if the pacer is programmed to generate it, the programmed coupled interval represents either a fixed time (if the programming disables scanning of the coupled interval), or it represents the maximum coupled interval (if the programming calls for scanning of the coupled interval). In the latter case, the programmed coupled interval is the first value used when the pacer functions for the first time after the initial programming; thereafter, the scanning begins with the retained successful value. There are 15 coupled interval values from which the physician can choose, 125, 140, 160, 180, 200, 210, 230, 250, 270, 290, 300, 320, 340, 360 and 380 milliseconds, and thus four bits are required to represent them.

The sixth parameter which can be programmed is "tachy rate"; this is the parameter which determines the width of the pulse generated by monostable multivibrator MN1 (FIG. 9) each time that a heartbeat is detected. Four bits are used to represent the tachy rate, and the eight possible values are 40, 130, 140, 150, 165, 180, 200 and 225 beats per minute. For example, if a tachy rate of 150 beats per minute is selected, the pulse width of the multivibrator is adjusted such that the Q output of the multivibrator will remain high if, after any beat, four successive beats are detected at a rate which exceeds 150 beats per minute, with the inter-beat interval between any two successive beats not exceeding 60/150 or 400 milliseconds.

The program controller chip IC5 responds to incoming reed switch pulses in four programming steps. Although the four steps will be described in a particular sequence, the first three can be interchanged; it is only the fourth step which must always be the fourth step in a programming sequence.

There are seven output conductors from chip IC5, labeled A-F and L. These outputs are connected to seven inputs of chip IC4, the inputs bearing similar letter designations. The seven inputs to chip IC4 appear at the top of FIG. 3, FIGS. 3 and 4 showing the details of chip IC4. The A-D inputs are data bits which represent parameter values. The E and F inputs are address bits which select particular latches for the storage of the data bits. Input L is a latch control input. The program controller chip IC5 decodes incoming reed switch pulses, and applies two address and four data bit values to its outputs A-F. The chip then applies a positive pulse to the L output which actually controls latching of the data bits in a set of latches determined by the address bits. (The program controller chip IC5 also sets an impedance value at its output pin 12, but this occurs during the fourth programming step, and will be described below.)

The first programming step involves setting the tachy rate. The four bit values which represent the rate and appear on conductors A-D are applied to the D inputs of register flip-flops D1-D4 on FIG. 3. The E and F address bits are both low during this step, and consequently the output of gate G1 is high to enable one input of gate G2. When the latch pulse is applied to the other input of gate G2 over conductor L, the gate output goes low. This output is coupled to the clock input of each of the four flip-flops. At the end of the latch pulse, the rising edge at the clock input of each flip-flop clocks the four tachy-rate data bits into the four flip-flops.

The second programming step involves storing the four bits which represent the initial delay in the latch which comprises register flip-flops D7-D10 on FIG. 3. The four data bits on lines A-D are connected to the D inputs of the flip-flops just as they are connected to the D inputs of flip-flops D1-D4. It is now gates G7 and G8 which control latching of the data in the flip-flops. The output of gate G8 is connected to the clock input of each of the flip-flops, and the latch input pin 6 is connected directly to one input of gate G8, just as it is connected to one input of gate G2. Just as the other input of gate G2 is connected to the output of gate G1, the other input of gate G8 is connected to the output of gate G7. One of the inputs of gate G7 is connected directly to the F address input, and the other input of gate G7 is connected through an inverter to the E address input. Thus an EF address of 10 causes the output of gate G7 to go high, and at the trailing edge of the latch pulse the initial delay data bits are clocked into flip-flops D7-D10.

In the third programming step, the four data bits which represent the coupled interval are latched into register flip-flops D11-D14. Gates G13, G14 control the latching of the data bits in these flip-flops just as gates G1, G2 and G7, G8 control latching of the data bits in the two other sets of latches during the first and second programming steps. It will be noted, however, that both inputs to gate G13 are now derived from inverters which are connected to the E and F address inputs. Consequently, in the third programming step the E and F outputs of chip IC5 are both high.

As mentioned above, the order in which the first three programming steps occur is unimportant, as long as the four data bits to be latched during each step are accompanied by E and F address bits which identify the respective one of the three sets of latches.

During the fourth (necessarily the last) programming step, all of the rest of the programming information described generally above is latched. The sensitivity of the sense amplifier/comparator chip IC1 is determined by a single bit which controls an external resistor connection to pin 12 of chip IC5. Pin 12 is coupled to the input filter circuit for chip IC1, and it directly controls the sensitivity of chip IC1 as is standard in the pacer art. The reason that the fourth programming step must always be the last one is that a separate latch is not provided for the sensitivity control. Chip IC5 itself serves as the sensitivity latch.

During the last programming step, the E and F address bits represent a 01 combination. It will be noted that the E address bit input on FIG. 3 is connected directly to one input of gate G3, and the F address bit input is connected through an inverter to the other input of gate G3. The output of gate G3 is connected to one input of gate G4, the other input to which is connected to latch input pin 6. Consequently, gate G4 clocks flip-flops D5 and D6 at the end of the latch pulse. The A and B data bits are connected to the D inputs of these two flip-flops, and these two data bits represent the four pulse width values (off, and 0.25), 0.35 and 0.6 milliseconds). The two pulse-width bits are stored in the two flip-flops during the last programming step.

The last two pieces of information required by the pacer are two bits which represent whether a second stimulus is to be generated at all and, it it is, whether the coupled interval is to be fixed or scanned. These two data bits appear at the C and D outputs of program controller chip IC5. Separate latches are not provided, and instead chip IC5 serves as the latch for these bits just as it does for the sensitivity control. Referring to FIGS. 1 and 2, it will be noted that pins 9,10 of chip IC5 are connected directly to pins 10,11 of chip IC3. Referring to FIG. 7 (part of chip IC3), it will be seen that input pins 10,11 of chip IC3 are connected to output pins 9,10 of chip IC5. If the program controller chip IC5 maintains a low potential (a 0) at its output pins 9,10, then only a single stimulus is generated following each tachycardia confirmation. On the other hand, a high level (a 1) controls the generation of a second stimulus as well.

In a similar manner, output pin 11 of chip IC5 is connected to input pins 16,17 of chip IC3 (see FIGS. 1 and 2). This connection is also shown on FIG. 7 (part of chip IC3). If the latched potential at outpin pin 11 of chip IC5 represents a 0, then the coupled interval is scanned, and if it represents a 1, the coupled interval remains fixed at the value latched in flip-flops D11–D14 (FIG. 4).

In the description of monostable multivibrator MN1 (FIG. 9) above, it was explained that pins 1 and 2 of chip IC3 (see FIGS. 2 and 5) are connected to the junction of capacitor C9 and a resistor chain. The resistor chain is shown generally by the symbol R on FIG. 9, but actually comprises resistors R17, R18B, R18A, R19, R20 and R21 (see FIG. 2). The tachy-rate flip-flops D1–D4 on FIG. 3 have their Q and $\bar{Q}$ outputs connected to respective inputs of transmission gates TG1–TG4. Each gate, when turned on, shorts a pair of pins to each other, the five pins 7–11 being connected to the various resistors in the resistor chain just described. Thus if all of the transmission gates are off, all of the resistors are in the chain. On the other hand, when any two adjacent output pins are shorted to each other through a respective transmission gate, the resistor or resistors connected between the two pins are shorted and do not contribute to the total impedance. It is in this manner that the four tachy-rate flip-flops determine the minimum rate which must be exceeded for tachycardia confirmation, the physician being able to select from among eight different rates (one of which is "artificial" in that it is not really a legitimate tachy rate, but rather is programmed in order to attempt to induce tachycardia).

Chip IC2 on FIG. 1 generates the stimulating pulses, as will be described below. The width of each pulse is controlled by the potential which appears at input pins 11,12. Pins 11,12 are connected to the junction of resistors R14, R15 and R16. While resistor R14 is connected to the positive supply rail, the other two resistors are connected to output pins 12 and 13 of chip IC4. These two output pins, together with output pin 23 and pulse-width flip-flops D5 and D6 (FIG. 3), determine the pulse width.

Each of pins 12,13 and 23 is either floating or held at the potential of the positive supply ($V_{DD}$ at pin 14, FIG. 3). If both of flip-flops D5 and D6 have bits of value 1 stored in them, their Q outputs are both high. Since both Q outputs are connected to inputs of gate G6, the output of gate G6 is low and the connected P-channel transistor between pins 14 and 23 is held on. Consequently, the positive potential at pin 14 is extended to on/off pin 23. Referring to FIGS. 1 and 2, it will be noted that pin 23 of chip IC4 is connected through resistor R7 to pin 2 of chip IC2. Whenever the potential at pin 2 is high, no pulses are generated by chip IC2. Consequently, when a data bit combination of 11 is stored in flip-flops D5 and D6, the device is inhibited from operating. For each of the other three combinations of data bits, the output of gate G6 is high and pin 23 floats. Pacer pulses can be generated, and the pulse width depends on the potentials which appear at pins 12 and 13.

When each of flip-flops D5,D6 contains a 0, the two inputs of gate G5 are low, and its output is high; the P-channel transistor connected between pins 12 and 14 is off so pin 12 floats. Since the $\bar{Q}$ output of flip-flop D6 is high in such a case, the P-channel transistor between pins 13 and 14 is also off, and pin 13 floats. Referring to FIG. 2, resistors R15,R16 are effectively out of the circuit, and the only connection to pins 11,12 of chip IC2 is that of resistor R14 whose other end is connected to the positive supply rail.

With a 1 in flip-flop D5 and a 0 in flip-flop D6, pin 13 still floats. But the output of gate G5 is now low so that pin 12 is connected to the positive supply at pin 14. Referring to FIG. 2, resistor R15 is now effectively in parallel with resistor R14 between pins 11,12 of chip IC2 and the positive supply.

The last case is that in which flip-flop D5 contains a 0 and flip-flop D6 contains a 1. The output of gate G5 is once again low due to one of its inputs being connected to the Q output of flip-flop D6. The $\bar{Q}$ output of the same flip-flop is low. Consequently, both of pins 12,13 are connected to pin 14 through their respective coupling transistors. Effectively, all of resistors R14, R15 and R16 are connected in parallel between pins 11,12 of chip IC2 and the positive supply, to provide the third possible pulse width.

Referring to FIG. 2, output pins 12,13,14,18 and 7 of chip IC3 will be described below as selectively controlling the shorting out of resistors in a series chain comprising resistors R9–R13. One end of the resistor chain is connected to ground (either through resistor R13, or directly through pin 12 of chip IC3 when the chip grounds the pin). The resistor chain then continues from the junction of pin 7 and resistor R9 to resistor R25. In a similar manner, resistors R22–R25 are connected in series in the overall chain, with selected ones of the four resistors being shorted out depending upon whether pin pairs such as 18,19 are internally shorted in chip IC4. The resistor chain terminates in resistor R8 which is connected to capacitor C8. The resistor chain and the capacitor control the timing of chip IC2, that is, when a stimulating pulse is generated. The same resistor chain is used to control the timing of both the first stimulus and the second stimulus (where required) and thus the same resistor chain determines both the initial delay and the coupled interval. It is chip IC3 which shorts out selected resistors from among those in the group R9–R13 to control scanning of both the initial delay and the coupled interval; as different pairs of pins among pins 12,13,14,18 and 7 are shorted to each other during the scanning of both the initial delay and the coupled interval, both time periods decrease in 6-millisecond discrete steps. But the maximum time periods (when none of resistors R9–R13 are shorted) are controlled by chip IC4 and the selective shorting of resistors R22–R25. The circuitry on FIG. 4 (part of chip IC4) selectively shorts pairs of adjacent pins among pins 17–21 in order to control the maximum initial delay and the maximum coupled interval. The control is exercised by flip-flops D7–D10 or flip-flops D11–D14, depending upon whether it is the initial delay or the coupled interval which is to be timed. The same resistors are used for both types of control since the two types of timing come into play at different times during each cycle.

Output pin 20 of chip IC3 (FIG. 2) is connected over the IPC conductor to input pin 15 of chip IC4. Output pin 19 of chip IC3 is connected over the CPC conductor to input pin 16 of chip IC4. Both output pins are normally high in potential. Whenever an initial delay is to be timed, chip IC3 causes IPC pin 20 to go low; conductor IPC is the initial-delay pulse control. Similarly, whenever a coupled interval must be timed, chip IC3 causes its pin 19 to go low; conductor CPC is the coupled-interval pulse control. Referring to FIG. 4, when no timing is required, and both of the IPC and CPC conductors are high in potential, the outputs of all of gates G9–G12 and G15–G18 are low. Thus the inputs of all of gates G19–G22 are low, and all of these gate outputs are high. The high potentials hold off the four respective transmission gates which are connected between respective pairs of pins in the group comprising pins 17–21.

When an initial delay must be timed, conductor IPC goes low. Thus the IPC inputs to gates G9–G12 have no effect on the circuit operation, and the gate outputs depend upon only the data stored in flip-flops D7–D10, since the $\overline{Q}$ outputs of these flip-flops are connected to respective inputs of the gates. Since the outputs of gates G15–G18 remain low because the CPC conductor is high in potential, these gates do not affect the operations of gates G19–G22. The latter gates are now controlled by the outputs of gates G9–G12, that is, the data bits stored in flip-flops D7–D10. It is in this manner that this group of flip-flops controls the selective shorting of resistors R22–R25 to set the maximum initial delay. During successive cycles, it is resistors R9–R13 which are selectively shorted out so that the initial delay decreases in 6-millisecond decrements. The combination of resistors R22–R25 which is involved in the initial delay timing is always the same whenever the timing takes place, the combination being controlled by the data latched in flip-flops D7–D10.

Similar remarks apply to the longest coupled interval (the only coupled interval if there is no scanning). With the IPC conductor high and the CPC conductor low on FIG. 4, it is now flip-flops D11–D14 which control the operations of gates G19–G22 and consequently which of resistors R22–R25 are placed in the resistor chain when coupled interval timing is required. The same pre-selected set of resistors is always used for the coupled interval timing; the 6-millisecond decrements in the case of a scanned coupled interval are controlled by chip IC3 shorting out a different combination of resistors R9–R13 during successive cycles.

Brief Description of Chips IC1 and IC2

Before proceeding to a detailed description of the overall system, it will be helpful to review the operations of chips IC1 and IC2. Both of these chips (1438B and 1400R) are commercially available devices and they perform standard functions. For this reason, it will suffice to describe the input and output signals of the two chips, without describing how they work internally.

The two electrode connections (IND and STIM) are shown on the left side of FIG. 1. The indifferent electrode is grounded. The stimulating electrode is coupled both to pins 20,21 of chip IC1 and to pins 9,10 of chip IC2. Chip IC1 is a standard sense amplifier/comparator which serves to detect a heartbeat. As described above, the sensitivity is determined by program controller chip IC5 (pin 12). The components connected to chip IC1 are all standard, and the sense amplifier/comparator operation is the same as that to be found in prior art pacers. Whenever a heartbeat is detected, a positive pulse appears at output pins 9,10.

Chip IC2 is a timing oscillator. It is the "heart" of a conventional pacer, but is used in the illustrative embodiment of the invention only as a timer and pulse generator. A positive pulse appearing at pins 21,22 is internally coupled through the chip to pins 19,20. The pulse is coupled through capacitor C6 to pins 17,18. A trigger input at pins 17,18 resets the internal oscillator in chip IC2 and starts a new timing cycle. Chip IC2 can operate in either the synchronous or the inhibit mode. In the former a stimulating pulse is generated at pins 9,10 whenever a heartbeat is detected in order to reinforce it, and in the latter such a reinforcement pulse is not generated. Because pin 1 is grounded, chip IC2 operates in the inhibit mode.

If a positive potential is applied through resistor R6 to capacitor C6, the trigger pulses are not extended from pins 19,20 through the capacitor. Thus when pin 6 of chip IC3 (FIG. 2) is high, it inhibits the detection of heartbeats. A low potential applied to pins 17,18 also prevents the trigger inputs from resetting the timer. When reed switch RS1 is operated, the low potential applied through "hot carrier" diode D2 to pins 17,18 causes the oscillator in chip IC2 to run free and pacing pulses to be generated continuously. (The term "hot carrier" refers to the fact that the voltage drop across the diode is 0.3 volts, not the usual 0.6 volts.) The pulses are in fact not generated continuously, but the reason will be described below.

Pacing pulses are generated at pins 9,10 of chip IC2, and are coupled through capacitor C5 to the stimulating electrode. Coincident with each pacing pulse, a negative pulse is generated at pins 3,4.

A negative pulse is also generated at pins 15,16 whenever a pacing pulse is delivered to the stimulating electrode, just as a negative pulse appears at pins 3,4. However, a negative pulse also appears at pins 15,16 whenever a heartbeat is detected, in which case a negative pulse does not appear at pins 3,4 since chip IC2 is operated in the inhibit mode. Capacitor C4 is the charge storage capacitor which discharges through pins 9,10 whenever a stimulating pulse is required. Capacitor C8, connected between pin pairs 15,16 and 13,14 is the rate timing capacitor. This capacitor, as well as resistor R8 and all of the resistors previously described in the resistor chain, determine the rate at which the internal oscillator of chip IC2 operates.

The potential at pins 11,12 of chip IC2 controls the width of each pulse which is generated, as described above.

Lastly, a high potential applied to pin 2 of chip IC2 disables the chip from generating pacing pulses at all. When pin 23 of chip IC4 (FIG. 2) is high in potential, as described above, the potential extended over the on/off conductor and through resistor R7 prevents pacing pulses from being generated. Capacitor C7 is normally charged through resistors R26, R4 so that it also normally inhibits pulse generation. Chip IC2 is thus held off most of the time. When a stimulus is required, capacitor C7 is discharged through diode D3 and resistor R31, as will be described below.

With these remarks in mind, the system operation will now be described. The system logic is controlled by chip IC3. In the following description reference should be made to FIGS. 5–8 (chip IC3), as well as to FIGS. 1 and 2 which depict the connections from chip IC3 to the remainder of the system. It should be noted that two pin connections to chip IC3 are not shown. These pin connections are merely test points and are not involved in the system operation; they are omitted from the drawing for the sake of clarity. Pin 3 of chip IC3 is in fact connected to the Q output of multivibrator MN1, shown in block form on FIG. 5 and in detail on FIG. 9. Pin 9 of chip IC3 is the output of an inverter, also not shown, whose input is connected to the output of inverter 59A at the lower right corner of FIG. 8.

System Operation

When a heartbeat is detected, a negative pulse appears at pins 15,16 of chip IC2, as described above. This pulse is extended to pin 5 of chip IC3, as shown in FIGS. 1 and 2. The negative pulse is inverted by inverter 1 (FIG. 5) and a positive pulse is applied to the trigger (A) input of the monostable multivibrator. A positive pulse now appears to the Q output of the multivibrator, its duration being dependent upon the "tachy rate" programmed by the physician (see description above of chip IC4 and resistors R17-R21). The Q output is connected to one input of gate 4. The same pulse which triggers the multivibrator is applied to a second input of gate 4. The third gate input is connected to the output of inverter 7B which is normally high in potential. Thus as long as the output of inverter 7B is high, the output of gate 4 is pulsed low whenever a heartbeat is detected.

Flip-flops 5,6 and 7 comprise a standard ripple counter which is initially reset to 000. With the $\overline{Q}$ output of each of flip-flops 5 and 7 initially high, and since they are connected to inputs of gate 7A, the gate output is low. The output is inverted by inverter 7B to apply a high potential to the third input of gate 4.

Flip-flop 5 is toggled on the trailing edge of each output pulse from gate 4. If the counter is not reset, as successive heartbeats are detected and the counter cycles from 000 to 100, the $\overline{Q}$ output of at least one of flip-flops 5 and 7 remains high, and the output of gate 7A remains low. But when the fifth pulse is counted without the counter having been reset during the sequence, the $\overline{Q}$ output of each of flip-flops 5 and 7 is low, and the output of gate 7A goes high. The output of inverter 7B now goes low to disable gate 4; no further pulses are counted.

The Q output of multivibrator MN1 is connected to an input of gate 10. Whenever the multivibrator times out, that is, the Q output goes low without the output pulse being extended by the arrival of another trigger input before the time-out is over, one input to gate 10 goes low. The output of gate 7A is connected to the other input of gate 10, and this input is thus low in potential until five heartbeats have been counted. Thus each time-out of the multivibrator, as long as the counter has not reached a count of five, causes the output of gate 10 to go high.

One input of gate 9 is connected to the output of inverter 14, whose input is connected to the output of gate 37. As will be described below, the output of gate 37 is normally high, and thus one input to gate 9 is normally low. Consequently, whenever the Q output of the multivibrator goes low at the end of a time-out and the output of gate 10 goes high, the output of gate 9 goes low, and the output of inverter 9A goes high. Since the gate output is connected to the reset input of each flip-flop in the counter, this causes the three-stage counter to reset to 000.

Thus whenever a heartbeat occurs after a preceding heartbeat with an inter-beat interval longer than the reciprocal of the "tachy rate", the counter is reset and the tachycardia confirmation cycle starts all over again. But if five rapid heartbeats are detected in succession, the Q output of the multivibrator does not go low to reset the counter. Even though it may go low after the fifth beat is counted, the output of gate 7A is now high and it is connected to an input of gate 10; thus the output of inverter 9A is locked low as soon as a count of five is reached so that the counter cannot be reset even if the multivibrator times out.

The tachycardia confirmation test involves four rapid beats, not five, even though five beats are counted. The first beat merely serves as a time reference for the second. The basic test is whether four rapid beats occur in succession, each of which is too soon after the respective previous beat. Once tachycardia is confirmed, the counter remains at a count of five and further counting is inhibited. The low potential which is now at the output of inverter 7B holds gate 4 off.

This same potential is inverted by inverter 3 and thus a positive potential appears at pin 6 of chip IC3 (FIG. 5). As indicated on the left of FIG. 5, and as shown in FIGS. 1 and 2, the positive potential is extended through resistor R6 to pins 19,20 of chip IC2. Any further heartbeats which are detected by chip IC1 are thus ignored. Also, since the count of five was reached in the first place by a negative pulse appearing at pin 5 of chip IC3, which pulse resulted from chip IC2 having detected a heartbeat and generated a negative pulse at pins 15,16, the oscillator on chip IC2 starts timing a new cycle. As will become apparent, this timing determines the initial delay, following which chip IC2 generates a first stimulus. The reason for inhibiting heartbeat detection in chip IC2, by holding pins 19,20 high as just described, is that the oscillator on chip IC2 is used to determine when the stimuli should be applied, and this timing function should not be interfered with by any heartbeats which may occur.

When the output of gate 7A first goes high, several things happen in addition to those described above. First, gate 29 is enabled since one of its inputs is now high. (Its other input, however, is still low.) Second, the positive potential is inverted by inverter 7C, and inverted once again by inverter 58B to clock flip-flop 58. Since the D input of the flip-flop is connected to the positive supply, the flip-flop is set and its Q output goes high to enable gate 57. Third, the positive potential which now appears at the output of inverter 59A is applied to the second input of gate 57 and also to the gate of transistor 56. The transistor turns on, and the output of gate 57 goes low.

The output of gate 57 is the IPC conductor which, as shown on FIG. 2, is extended from pin 20 of chip IC3 to pin 15 of chip IC4. It will be recalled that when the IPC conductor goes low, chip IC4 (FIGS. 4 and 5) shorts out pre-selected ones of resistors R22-R25 for controlling the programmed (longest) initial delay. It will also be recalled that capacitor C7 on FIG. 1 is initially charged to a positive potential, the positive potential at pin 2 of chip IC2 preventing the generation of stimulating pulses. Now that a stimulus is required, however, a low potential must be applied to pin 2 of chip IC2. Because conductor IPC is now low in potential, capacitor C7 discharges through diode D3 and resistor R31 so that a stimulus can be generated.

Referring to FIGS. 1 and 2, the overall resistor chain involved in all timing functions of chip IC2 consists of resistors R9-R13, R22-R25 and R8, different ones of the resistors having shorted out at different times. With transistor 56 on FIG. 8 now on, pin 12 of chip IC3 is grounded. As shown on FIG. 2, this shorts our resistor R13 from the resistor chain. The actual initial delay which is now timed depends upon two sets of resistors, R9–R12 and R22–R25. The latter set is pre-selected and the same resistors are always placed in the chain whenever an initial delay is to be timed. If all of the resistors R9–R12 are included in the chain, then the pre-selected combination of resistors R22–R25 provides the longest initial delay, as programmed by the physician. But the actual initial delay in any cycle is determined by which of resistors R9–R12 happen to be shorted, i.e., how many 6-millisecond decrements have already taken place. Depending upon the total impedance of the resistor chain, the oscillator on chip IC2 times out and results in the generation of a first stimulating pulse. Coincident with this pulse, and as described above, a negative pulse is generated at pins 3,4 on chip IC2. This pulse is coupled through resistor R30 on FIG. 1 to pin 8 of chip IC3. As shown on FIG. 8, the negative pulse at pin 8 is inverted by inverter 68 and thus resets flip-flop 58. Gate 57 now turns off, and it is gate 59 whose CPC output now goes low.

As described above, when the CPC conductor goes low, a different combination of resistors R22–R25 is included in the resistor chain. Since the oscillator on chip IC2 is still free running as a result of pins 19,20 being held high (assuming that the second stimulus is to be generated), the coupled interval timing now takes place. Chip IC3 selects some other combination among resistors R9–R12 depending on how many decrements of the coupled interval have already taken place, as will be described below, but the resistors controlled by chip IC4 and the CPC signal (FIG. 4) are such that should all of resistors R9–R12 be included in the chain, the longest coupled interval will be timed. At the end of the interval, a second stimulus is generated.

Chip IC2 can generate a second pulse only if pin 2 is not held high to disable pulse generation. It is the IPC conductor going low which discharges capacitor C7 rapidly to permit the first pulse to be generated. Although the IPC conductor goes high when the CPC conductor goes low, capacitor C7 charges through the high-impedance resistor R4. The capacitor cannot charge fast enough to inhibit the generation of a second pulse even for a coupled interval of maximum duration.

Assuming that a second pulse is to be generated, pins 10,11 on FIG. 7 are high in potential as described above. As soon as the Q output of flip-flop 58 goes high upon tachycardia confirmation, both inputs of gate 47 are high, its output goes low, and the output of inverter 47A goes high to reset flip-flop 45. The low potential at the Q output of the flip-flop disables gate 37, whose output remains high. The flip-flop output is initially high because the output of inverter 46 is low, the input to the inverter normally being held high by the high potential at pins 3,4 of chip IC2. Even though the negative input pulse at pin 8, which pulse is coincident with the first stimulus, is inverted by inverter 46 so that a positive pulse is applied to the other input of gate 37, the gate output remains high since flip-flop 45 is still reset.

The negative pulse at pin 8 is coupled to one input of gate 49. Since the other input to the gate is connected to the low Q output of flip-flop 45, the output of gate 49 goes high with the generation of the first stimulus. A negative pulse thus appears at the output of inverter 48, and flip-flop 45 is clocked on the trailing edge of the pulse; by this time flip-flop 58 has been reset so as to lift the reset from flip-flop 45. The Q output of flip-flop 45 thus goes high at the end of the pulse at pin 8, after the short switching time of the flip-flop. Although one input of gate 37 is thus now held high, the output of inverter 46 is low once again since the pulse at pin 8 has terminated. Thus the first stimulus results in the setting of flip-flop 45 but the output of gate 37 remains high.

The pulse at pin 8 which is coincident with the second stimulus has no effect on flip-flop 45, the flip-flop remaining set until the next tachycardia confirmation at which time flip-flop 58 is set once again and gate 47 causes flip-flop 45 to reset. But the second pulse at pin 8, through inverter 46, causes the output of gate 37 to now go low and the output of inverter 14 to go high. The output of gate 9 thus goes low and the output of inverter 9A goes high in order to reset the ripple counter which comprises flip-flops 5–7. Since two pulses have been delivered, the system now starts looking for a tachycardia episode all over again, in order to determine whether another pair of pulses must be generated. Toward this end, monostable multivibrator MN1 is reset by the negative pulse at the output of gate 37, after inversion by inverter 2A.

If only a single stimulus is to be generated, pins 10,11 on FIG. 7 are low. Consequently, the output of gate 47 is high and the output of inverter 47A is low so that flip-flop 45 is not reset by the setting of flip-flop 58. The Q output of flip-flop 45 remains permanently high. The first negative pulse at pin 8, which pulse is coincident with the first stimulus, results in the output of gate 37 going low. The 3-bit counter comprising flip-flops 5–7 is thus reset after the first stimulus is generated. Flip-flop 58 is also reset by the first negative pulse at pin 8 and its $\overline{Q}$ output goes high to enable one input of gate 59. However, the other input is derived from the output of gate 7A which now goes low once again with the resetting of flip-flops 5 and 7. Consequently, even though flip-flop 58 is reset, the output of gate 59 does not go low; the CPC conductor remains high and there is no timing of a coupled interval.

Reed switch RS1 on FIG. 1 is connected to pin 15 of chip IC3. Referring to FIG. 6, it will be noted that each time the reed switch is operated and a ground potential appears at pin 15, inverters 26 and 26A apply positive reset pulses to all of flip-flops 22–25 and 60–63. As will be described below, these are the flip-flops which control the decrementing of the initial delay and the coupled interval by 6-millisecond decrements. During programming, each time the reed switch is operated all of the flip-flops are reset. This has the effect of inserting all of resistors R9–R12 (FIG. 2) in the resistor chain so that the longest (programmed) initial delay and coupled interval are first timed. Whenever a cycle does not result in tachycardia termination, flip-flops 22–25, which are arranged as a four-bit counter register, have their count incremented so that in the next cycle the initial delay is decremented by 6-milliseconds. After the fifteenth decrement, the initial delay is set to its highest value once again, as the counter cycles from 1111 to 0000. On alternate resettings of flip-flops 22–25, the similar counter register which comprises flip-flops 60–63 is incremented so that the coupled interval is decremented by 6 milliseconds.

It is gate 21 which controls the incrementing of the counter which comprises flip-flops 22–25. The count representing the number of 6-millisecond decrements of the initial delay is incremented whenever the output of gate 21 goes high. It is important that gate 21 not operate immediately after the one or two required stimuli are generated. That is because if tachycardia has been terminated, the count in flip-flops 22-25 should be retained so that the same initial delay and coupled interval values will be used when the next tachycardia episode is confirmed; downward scanning of the initial delay and the coupled interval always begin with the two last successful values. (It is only when a tachycardia episode is encountered following initial programming that the scanning begins with the maximum initial delay and the maximum coupled interval, since all of flip-flops 22-25 and 60-63 are reset.)

Gates 15-20 comprise a standard D-type flip-flop. The output of gate 17 is the Q output of the flip-flop, and the output of gate 20 is the $\bar{Q}$ output. The set input, applied to inputs of gates 16 and 19, is derived from the Q output of multivibrator MN1, and the reset input is derived from the output of gate 37. The reason for the rather complicated form of flip-flop is that it must be set by the rising edge of the pulse at the $\bar{Q}$ output of the multivibrator, and the rising edge is not necessarily sharp; the flip-flop which is used, standard in the art, can be set even on a slowly rising edge.

The flip-flop is reset when the output of gate 37 goes low. This is after the first stimulus has been delivered if the pacer has been programmed not to deliver a second, or after the second stimulus has been delivered if the pacer has been programmed to deliver a second stimulus as well as a first. When the flip-flop resets, the Q output (output of gate 17) goes low, this output serving as one input to gate 21. The output of inverter 7B is connected to a second input of gate 21. This output is low during the initial delay and coupled interval timing periods, but when gate 37 controls the resetting of the flip-flop comprising gates 15-20, it also controls resetting of the counter comprising flip-flops 5-7. As soon as the latter flip-flops reset, the output of gate 7B goes high. Thus, the output of gate 21 remains low even though the output of gate 17 no longer holds it low.

Gate 21 should not operate to increment the counter which comprises flip-flops 22-25 because when the tachycardia confirmation circuit is first enabled to operate once again, there is no way of knowing whether tachycardia has yet been terminated. If it has been terminated, the output of gate 21 should remain low so that flip-flop 22 is not toggled. In the event the output of gate 17 goes low before the output of inverter 7B goes high, two inputs to gate 21 would be low, and the output would go high to toggle flip-flop 22. In order to prevent this, the output of gate 37 is coupled through inverter 14 to a third input of gate 21. While the output of gate 37 is low the output of inverter 14 is high, so that the output of gate 21 remains low. By the time the output of gate 37 goes high once again, the output of inverter 7B has gone high so that it can hold the output of gate 21 low.

Thus by the time that the output of gate 37 reverts to its normally high state, the tachycardia confirmation circuit is enabled to operate once again, and the flip-flop which comprises gates 15-20 is reset with the output of gate 17 being low. If tachycardia has not been terminated, the multivibrator MN1 does not time out as it is continuously re-triggered by heartbeats which are once again detected (since pin 6 on FIG. 5 is now low), and the $\bar{Q}$ output remains low after the first multivibrator triggering. Consequently, following the next tachycardia confirmation, when the output of inverter 7B goes low, all three inputs to gate 21 are low in potential and the output goes high to clock flip-flop 22. Since tachycardia has not been terminated, the initial delay which is now timed is decremented 6 milliseconds.

On the other hand, if tachycardia has been terminated, the multivibrator times out and the $\bar{Q}$ output goes high. The flip-flop comprising gates 15-20 is now set and the output of gate 17 goes high. Thus the output of gate 21 is held low. Even though another tachycardia episode may be confirmed some time later, when the output of inverter 7B goes low it does not result in the toggling of flip-flop 22. This allows the previously successful initial delay and coupled interval to be the first ones which are used.

It will be recalled that immediately upon tachycardia confirmation, the output of gate 7A goes high to enable one input of gate 29 (FIG. 5). The other input to this gate is connected to the output of gate 59, the CPC conductor, which is high in potential during the initial delay timing. Thus the output of gate 29 is low, and it enables the operation of each of gates 30-33. The outputs of these four gates are controlled by respective flip-flops 22-25, and the output of each of gates 30-33 is coupled to an input of a respective one of gates 39-42. Each of these latter gates has another input, but these other inputs have no effect during the initial delay timing. The CPC conductor which is high in potential causes the output of each of gates 50-53 to remain low.

The outputs of gates 39-42 are coupled to respective transmission gates 28, 35, 44 and 55. As seen on FIG. 2, these are the four gates which control the selective shorting of resistors R9-R12 at pins 7, 18, 14 and 13 of chip IC3. (Gates 28 and 35 each includes a P-channel and an N-channel transistor connected in parallel; because these gates control resistors in the middle of the resistor chain, a full drive may not be available to fully turn on a single N-channel device. By providing two opposite-type transistors in parallel, they compensate for each other, as is known in the art. Single-transistor gates 44 and 55 are sufficient to short out resistors R11 and R12 since these resistors are at the end of the chain, closer to ground potential.)

When flip-flops 22-25 represent a count of 0000, all of resistors R9-R12 are in the resistor chain. The resistors are weighted in the approximate ratio 1:2:4:8 so that as flip-flops 22-25 count in binary fashion, successive decrements of the initial delay are all the same.

Referring to FIG. 2, it will be recalled that resistor R13 is shorted out be transistor 56 (FIG. 8) immediately upon tachycardia confirmation. Resistor R13 is nominally 10M. In the absence of tachycardia, this artificially high resistor is placed in the resistor chain in order to make the time-out period of the oscillator in chip IC2 so high that no pacing pulses can be generated; even though pin 2 of chip IC2 is held high in the absence of tachycardia to prevent the generation of pacing pulses, chip IC2 also requires a resistive connection to pins 13,14. But when one or two stimuli must be generated, resistor R13 is removed from the circuit so that the only resistors which control initial delay and coupled interval timing are resistors R9-R12, R22-R25 and R8. The reason for providing resistor R8 is that if a minimum initial delay or coupled interval has been programmed, all of resistors R22-R25 are shorted out, and if all of resistors R9-R12 are similarly shorted out at the end of the scan of the initial delay or coupled interval, then there would be no resistance connected to pins 13,14 of chip IC2. Resistor R8 serves as the minimum resistance for controlling a minimum initial delay or minimum coupled interval when the counter which comprises flip-flops 22-25 or the counter which comprises flip-flops 60-63 counts all the way up to 1111 and shorts out all of resistors R9-R12.

If a second stimulus is to be provided, then as described above the CPC conductor (output of gate 59 on FIG. 8) goes low after the first stimulus is generated. The output of gate 29 is now high, the outputs of all of gates 30-33 are low, and thus flip-flops 22-25 have no effect on the outputs of gates 39-42. But because the CPC input to each of gates 50-53 is now low, the outputs of these gates are determined by the count contained in flip-flops 60-63. It is now these four flip-flops which determine which of resistors R9-R12 are included in the resistor chain for controlling the coupled interval.

Flip-flops 60-63 control the scanning of the coupled interval. The potential at pins 10,11 (FIG. 7) has already been described as controlling whether or not a second stimulus takes place at all. The description thus far has also taken into account the timing of the coupled interval in accordance with the count in flip-flops 60-63. There remains to consider how these flip-flops are cycled.

Cycling is not required at all if a fixed coupled interval is to be employed. In such a case, pins 16,17 (FIG. 7) are high in potential and the output of gate 67 is low. The output of gate 67A remains high to hold flip-flop 66 reset. Since the $\overline{Q}$ output of flip-flop is high, the output of gate 65 remains low. The output of gate 65 never exhibits a falling edge and flip-flop 60 is never toggled. All of flip-flops 60-63 are reset when the pacer is programmed. Consequently, all of resistors R9-R12 remain in the resistor chain during the coupled interval timing, and the coupled interval remains fixed at the programmed value. On the other hand, if the coupled interval is to be scanned, pins 16,17 are low in potential so that flip-flop 66 is not held reset and the output of gate 65 is not held low. The flip-flop is initially reset, however, following programming; the low potential at pin 15 (FIG. 6) when the reed switch closes is inverted by inverter 26A to control resetting of flip-flop 66 along with resetting of flip-flops 60-63.

In the presence of normal heartbeats, the output of gate 7A is low. Similarly, multivibrator MN1 keeps on timing out since heartbeats are occurring at a rate slower than the tachy rate; when the $\overline{Q}$ output of the multivibrator goes high at the end of each time-out, a set pulse is applied to the flip-flop comprising gates 15-20. The flip-flop is not reset because the output of gate 37 remains high, and thus the output of gate 20 remains low. Thus the output of gate 36 is high to enable an input of gate 67 so that flip-flop 66 remains reset.

Upon tachycardia confirmation, the output of gate 7A goes high and thus the output of gate 36 goes low so that the reset input of flip-flop 66 is no longer forced high. Assuming that tachycardia is not terminated, successive single pulses or successive double pulses are generated in successive cycles, and the output of gate 37 goes low at the end of each cycle. The flip-flop comprising gates 15-20 is continuously reset and, because the flip-flop is not set by the $\overline{Q}$ output of multivibrator MN1 going high, each time that the output of gate 7A goes high upon tachycardia confirmation gate 21 increments the count in flip-flops 22-25. The initial delay is scanned down to its minimum value, at which time flip-flops 22-25 represent a count of 1111. The four inputs of gate 38 are connected to the respective Q outputs of the four flip-flops, and at this time the output of the gate goes low. Although the output of gate 38 is coupled to one input of gate 65, the other input of gate 65 is connected to the $\overline{Q}$ output of flip-flop 66 which is high since the flip-flop is still reset. Consequently, the output of gate 65 still remains low.

If tachycardia is still not terminated, when the output of gate 7A next goes high gate 21 advances the count in flip-flops 22-25 from 1111 to 0000, and the output of gate 38 goes high once again. The positive step at the output of gate 38 clocks flip-flop 66 since it is applied directly to the C input and through inverter 66A to the $\overline{C}$ input. The flip-flop is now set and the $\overline{Q}$ output goes low. But the output of gate 65 still remains low since the output of gate 38 is now high. Consequently, another scan of the initial delay begins with the programmed value, without the count represented in flip-flops 60-63 being incremented.

During the last cycle of the next scan of the initial delay, however, when flip-flops 22-25 represent a count of 1111 and the output of gate 38 is low, both inputs to gate 65 are low and its output is high. If tachycardia is not terminated during this cycle, gate 7A goes high in the usual way upon the next tachycardia confirmation. As soon as flip-flops 22-25 are cycled from 1111 to 0000 to begin a new scan of the initial delay, the output of gate 38 goes high once again and now the output of gate 65 goes low to exhibit a falling edge. This results in the clocking of flip-flop 60 and decrementing of the coupled interval by 6 milliseconds. When the output of gate 38 thus goes high for the second time, flip-flop 66 is clocked once again and it is now reset with the $\overline{Q}$ output going high. This holds the output of gate 65 low at the start of the next scan of the initial delay so that the coupled interval is not decremented even though gate 38 pulses once again. The net result is that the coupled interval is decremented by 6 milliseconds only at the start of every other scan of the initial delay.

The reason for this is that when the patient's heart has been beating normally but tachycardia is then confirmed, the scanning begins with the retained values of the initial delay and the coupled interval, stored in respective flip-flops 22-25 and 60-63. If tachycardia is not terminated, the initial delay is scanned down to the minimum value while the coupled interval remains at the previously successful value. Were the coupled interval to be decremented at the end of the first partial scan of the initial delay, there would be no scan of the higher value initial delays with the previously successful coupled interval. The first time that the maximum initial delay would be utilized at the start of the first complete scan, the coupled interval would be decremented and the previously successful value of the coupled interval would not be used at all until both the initial delay and the coupled interval would be scanned back to the point at which the coupled interval would be at the previously successful value. It is for this reason that the coupled interval is not decremented at the end of the scanning of the initial delay from the previously successful value to the minimum value. After this partial scan, a complete scan of the initial delay is controlled while using the previously successful coupled interval. It is only after this complete scan of the initial delay that the coupled interval is decremented.

The same operation ensues whether tachycardia is terminated during a scan of the initial delay which began with decrementing of the coupled interval, or during a scan of the initial delay at the beginning of which the coupled interval was not decremented. It makes no difference because upon tachycardia termination the output of gate 20 goes low while the output of gate 7A is low, and the output of gate 36 goes high to reset flip-flop 66.

It should be noted that the mechanism by which flip-flop 66 controls decrementing of the coupled interval only after every other complete scan of the initial delay is not really necessary during most of the cycling. It is only at the beginning of an overall scanning sequence that the coupled interval should not be decremented when flip-flops 22-25 are clocked to represent a count of 0000 for the first time. Thereafter, it is not necessary to control decrementing of the coupled interval only at the start of every other scan of the initial delay. It would be feasible, if desired, to allow the coupled interval to be decremented at the start of every scan of the initial delay, after there is at least one full scan of the initial delay with the previously successful coupled interval.

Most conventional heart pacers are designed so that a physician can determine the battery potential in order that the remaining life of the pacer may be ascertained. Often this is accomplished by placing a magnet over the patient's chest in the vicinity of the pacer, whereupon the closing of a reed switch causes the pacer to generate pulses at a continuous rate which is dependent upon the battery potential. But continuous pulses are not generated by a tachycardia control pacer. Thus there is no apparent way for the physician to determine the battery potential.

It would also be advantageous were there some way for the physician to ascertain the programmed values of initial delay and coupled interval. This is especially true in the case of a patient who consults a physician other than the one who programmed the device, in which case there may be no record of the programmed values. While the physician could monitor the ECG waveform of the patient and measure the maximum (programmed) values of initial delay and coupled interval, there is a problem with this approach. Even assuming that tachycardia can be induced so that stimuli are generated, a complete scanning cycle, that is, a complete scan of the initial delay and the coupled interval, typically takes longer than 10 minutes (allowing for tachycardia confirmation following each cycle). Since the scanning does not necessarily begin with the maximum initial delay and coupled interval, the physician may actually have to observe an ECG waveform for more than 10 minutes before the maximum initial delay can be ascertained. It would be highly desirable to provide a mechanism by which the programmed values could be determined rapidly.

There is one other capability which would also be advantageous and that is to provide a simple mechanism whereby the patient can completely inhibit operation of the pacer. The physician can accomplish this by programming the device so that pin 23 of chip IC4 (on/off) is high in potential, as described above. But if the patient is feeling discomfort, it is also advisable to provide him with a simple mechanism for disabling the pacer operation until the physician can program it off.

Flip-flops 12,13, transistor 8, and the several gate connections to pin 15 on FIG. 6 allow all of the aforesaid desirable features to be added to the pacer at little additional cost and with a minimum of complexity.

The reset inputs of flip-flops 12,13 of FIG. 6 are connected to pin 15. Thus during normal operation when reed switch RS1 (FIG. 1) is open, a positive potential is applied to the reset inputs of the flip-flops and they are held reset. But if a magnet is applied to close the reed switch, pin 15 is grounded through the switch so that the reset input to the flip-flops is lifted. The closing of the reed switch also serves two other functions. The first is to allow capacitor C7 to discharge through resistor R4. It will be recalled that the capacitor is normally charged through resistors R4 and R26 to prevent any pacing pulses from being delivered, the capacitor being discharged through diode D3 and resistor R31 when the IPC conductor goes low following tachycardia confirmation. In the same way, capacitor C7 discharges through resistor R4 and the reed switch to allow chip IC2 to generate pulses. Although resistor R4 is large in magnitude and capacitor C7 does not discharge quickly when the reed switch is closed, that is of no moment; as will be described, the desired operation is the generation of a pair of pulses and what is important is the time between the two pulses, not when the first one occurs. (It should be observed that if the on/off conductor is high in potential, capacitor C7 remains charged through resistor R7 which is of much lower magnitude than resistor R4, and chip IC2 cannot generate any pulses even if the reed switch is closed. If the pacers has been programmed off, it remains off even if the read switch is closed by a magnet.)

The other function performed by the reed switch is the pulling low of pins 17,18 of chip IC2 through diode D2. When these pins go low, chip IC2 operates in a free-running mode.

Eventually, capacitor C7 discharges through resistor R4 and chip IC2 starts to deliver pacing pulses at pins 9,10. With the delivery of each pulse, pins 3,4 go low as described above. In the usual way, a negative pulse is applied to pin 8 of chip IC3 (FIG. 8). Each negative pulse is inverted by inverter 11B and thus a positive pulse is applied to one input of gate 11 on FIG. 6. With flip-flops 12,13 being initially reset (as a result of pin 15 having previously been held high when the reed switch was open), the $\overline{Q}$ output of flip-flop 13 is high and thus the second input of gate 11 is enabled. When the output of gate 11 is pulsed low with the delivery of the first pulse from chip IC2, flip-flop 12 is set on the trailing edge. Flip-flops 12,13 comprise a standard two-bit ripple counter. The next pacing pulse results in the clocking of flip-flop 12 once again, since the $\overline{Q}$ output of flip-flop 13 is still high to enable gate 11 when the pulse arrives. But at the trailing edge of the pulse, when flip-flop 12 is reset and flip-flop 13 is set, the $\overline{Q}$ output of the latter flip-flop goes low to disable gate 11. At the same time, gate 8 turns on and applies the positive battery potential to pin 4. Referring to FIGS. 1 and 2, it will be seen that this positive potential charges capacitor C7 through resistor R7, just as does pin 23 of chip IC4 when the pacer is programmed off. Consequently, chip IC2 delivers only two pulses at pins 9,10.

The time interval between the two pulses is controlled in the usual manner by the resistor chain connected to pins 13,14 of chip IC2. None of the resistors in the overall chain is shorted out. It will be recalled that pin 12 of chip IC3 (FIG. 2) shorts out resistor R13 during initial delay and coupled interval timing. The resistor is shorted out when pin 12 on FIG. 8 goes low under control of transistor 56, the transistor being turned on when the output of gate 7A goes high upon tachycardia confirmation. But there is no tachycardia confirmation now, so gate 56 remains off and resistor R13 is not shorted out. The low potential at pin 15 of chip IC3 (see FIGS. 1, 2 and 6) due to the closing of the reed switch applies a positive potential through inverters 26,26A on FIG. 6 to the reset input of each of flip-flops 22-25 and 60-63. With all eight flip-flops reset, the inputs to all of gates 39-42 are low, and all of the gate outputs are high to hold off gates 28, 35, 44 and 55. Consequently, all of resistors R9-R12 are similarly placed in the resistor chain.

Both of the IPC and CPC conductors on FIG. 8 are high since there has been no tachycardia confirmation. Referring to FIG. 4, the inputs of all of gates G19-G22 are low, all of the gate outputs are high, and thus none of pins 17-21 are shorted to each other. Consequently, all of resistors R22-R25 remain in the resistor chain.

The net result is that the time interval between the two pulses generated by chip IC2 is the maximum, and is determined primarily by resistor R13. This maximum is selected so that the battery potential of 2.8 volts controls an inter-pulse interval of 1.5 seconds. As the battery potential decreases with age, the inter-pulse interval is reduced proportionally since it takes longer for capacitor C8 (FIG. 1) to charge. All the physician has to do is to observe the patient's ECG waveform and to time the interval between the two pulses in order to ascertain the battery potential. This is similar to the prior art technique of using a magnet to control the rate of a conventional heart pacer in order to determine the battery potential, inasmuch as the time interval between the two pulses which are generated is equivalent to a "rate". Of course, in order to achieve the effect with a tachycardia control pacer, it is necessary to artificially control the generation of at least two pulses in the manner described, even though chip IC2 does not function as an ordinary pacer.

It should be noted that a relatively high value of resistance is used for resistor R13 in order that the inter-pulse interval will vary between approximately 1.5 and 1.7 seconds as the battery ages. Two pulses which occur this far apart (the separation should be at least one second) can have no deleterious effect on the beating of the patient's heart.

The physician can use a magnet in the manner described in order to determine the battery potential. (In general, the time interval between the two pulses could represent some preselected pacer characteristic other than battery potential, e.g., the number of tachycardia episodes which have occurred if a suitable counter is provided.) But the patient can also use such a magnet to shut off the pacer so that it does not generate pulses even following tachycardia confirmation. Since pin 2 of chip IC2 is held at a high potential after two pulses are generated, for as long as the magnet is applied, the patient can hold the pacer off by holding the magnet in place. He may then go to see his physician (while still holding the magnet in place to keep the pacer off), and the physician can program the pacer permanently off by forcing pin 23 of chip IC4 high as described above. (Along the same lines, the patient might be furnished with a programmer of his own which would only be capable of programming the pacer off. Only the physician's programmer could control programming of the pacer on once again. A patient-operated pacemaker programmer of this type, although used for a completely different purpose, is disclosed in Loughman et al patent application Ser. No. 123,916 entitled "Patient-Operated Pacemaker Programmer", filed on Feb. 22, 1980, which application is hereby incorporated by reference.)

Upon removal of the magnet, flip-flops 12,13 on FIG. 6 are both reset once again when pin 15 goes high, transistor 8 turns off, and chip IC2 is no longer inhibited from generating stimulating pulses. The device operates in the usual way, as described above.

As described above, programming of the device results in the resetting of flip-flops 22-25 and 60-63; each reed closure resets the flip-flops through inverters 26,26A. Thus scanning always begins with the programmed values of initial delay and coupled interval since the decrement-controlling flip-flops are all reset. By monitoring the patient's ECG waveform and noting the time interval between tachycardia confirmation and the generation of a first stimulus, and the time interval between the first stimulus and the second, the physician can immediately determine the programmed values without having to wait for these values to be reached perhaps ten minutes later during the scanning. Of course, the physician can determine the time parameters quickly only if there is some way to induce tachycardia so that stimuli are generated in the first place. It is also advantageous to allow the physician to induce tachycardia so that he can observe whether the pacer is functioning at all, and also so that he can experiment with different programmed initial delays and coupled intervals to see which are most effective in terminating tachycardia.

A mechanism is therefore provided to induce tachycardia which does not require any additional components. It will be recalled that the tachy rates which can be programmed by the physician are all within the range 130-225 beats per minute, except for the lowest tachy rate of 40 beats per minute. The tachy rate of 40 beats per minute is not a "real" rate because even normal sinus rhythm results in tachycardia confirmation—normal heartbeats occur at a rate greater than 40 beats per minute. But by allowing such a low rate to be programmed, the physician may possibly induce tachycardia.

What happens is that a normal sinus rhythm results in tachycardia confirmation and the generation of one or two stimuli. Preferably, at the same time that the tachy rate is programmed to 40 beats per minute (without changing the initial delay and coupled interval parameters), the pacer should also be programmed to generate a second stimulus along with the first. The stimuli soon occur after five normal heartbeats and may actually induce tachycardia. It has been found that just as one or two stimuli shortly after a rapid heartbeat can terminate tachycardia, they can also induce it if the heart was beating in normal sinus rhythm. Once tachycardia is induced, the physician can observe the programmed time parameters if he so desires; scanning begins with the maximum values because the programming itself automatically resets flip-flops 22-25 and 60-63 (FIGS. 6 and 8). The physician may then reprogram the pacer to have a tachy rate which is in the "normal" 130-225 beat-per-minute range, along with the other parameters (including initial delay and coupled interval) whose combined efficacy is to be tested. By experimenting in this way, the physician can not only check the operation of the pacer, but he can also select optimum parameter values without the complications of further invasive surgery.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What we claim is:

1. A tachycardia control pacer comprising means for confirming a tachycardia episode, means for timing a time delay, means responsive to said confirming means for generating at least one heart-stimulating pulse at the end of said time delay following the last heartbeat to terminate said tachycardia episode, means for scanning said time delay through a range during successive cycles of operation of said pulse generating means, externally-controlled means for changing the range through which said time delay is scanned in accordance with externally-generated signals, and means responsive to operation of said externally-controlled means for causing the next time delay to be dependent upon only a time delay last represented by the externally-generated signals and independent of the last time delay controlled by said scanning means.

2. A tachycardia control pacer in accordance with claim 1 further including means under external control for causing the pacer to generate at least one pulse to induce tachycardia and for causing the next time delay to be dependent upon only the last time delay represented by the externally-generated signals.

3. A tachycardia control pacer in accordance with claim 1 wherein said externally-controlled means includes a switch connected to said pulse generating means operable by a magnet held in the vicinity of the pacer, and further including means for inhibiting operation of said pulse generating means only for as long as said magnet continues to be held in the vicinity of the pacer.

4. A tachycardia control pacer in accordance with claim 3 wherein said externally-controlled means is further operative to control the selective disablement or enablement of the generation of heart-stimulating pulses, and wherein said inhibiting means inhibits the generation of pulses temporarily until a programmed disablement can be effected.

5. A tachycardia control pacer in accordance with claim 1 wherein said externally-controlled means is further operative to control the selective disablement or enablement of the generation of heart-stimulating pulses, and further including externally-controlled means for temporarily inhibiting the generation of pulses until a programmed disablement can be effected.

* * * * *